(12) United States Patent
Haji Begli et al.

(10) Patent No.: US 11,548,863 B2
(45) Date of Patent: *Jan. 10, 2023

(54) PREPARATION OF HMF CATALYZED BY A MIXTURE OF SALT AND ACID

(71) Applicant: SÜDZUCKER AG, Mannheim (DE)

(72) Inventors: Alireza Haji Begli, Ramsen (DE); Christine Kröner, Kindenheim (DE); Kay Mantyk, Obrigheim (DE); Ralf Riemenschnitter, Carlsberg (DE)

(73) Assignee: SÜDZUCKER AG, Mannheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/058,530

(22) PCT Filed: May 28, 2019

(86) PCT No.: PCT/EP2019/063862
§ 371 (c)(1),
(2) Date: Nov. 24, 2020

(87) PCT Pub. No.: WO2019/229080
PCT Pub. Date: Dec. 5, 2019

(65) Prior Publication Data
US 2021/0214326 A1 Jul. 15, 2021

(30) Foreign Application Priority Data
May 29, 2018 (DE) .......................... 102018208510.2

(51) Int. Cl.
*C07D 307/54* (2006.01)
*C07D 307/50* (2006.01)

(52) U.S. Cl.
CPC ......... *C07D 307/54* (2013.01); *C07D 307/50* (2013.01)

(58) Field of Classification Search
CPC .................................................. C07D 307/54
See application file for complete search history.

(56) References Cited

U.S. PATENT DOCUMENTS 8,604,225 B2 * 12/2013 Pedersen ............. C07D 307/46
549/503
10,005,748 B2 * 6/2018 Vorlop ................. C07D 307/36

10,662,167 B2 * 5/2020 Kunz ................... C07D 307/50
2014/0349351 A1 11/2014 Jensen et al.
2015/0203461 A1 7/2015 Subramanian et al.

FOREIGN PATENT DOCUMENTS

| CN | 102399202 A | 4/2012 |
| CN | 104844543 A | 8/2015 |
| DE | 36 01 281 A1 | 7/1987 |
| DE | 10 2014 220 517 A1 | 4/2016 |
| WO | 2013066776 A1 | 5/2013 |
| WO | 2013106136 A1 | 7/2013 |
| WO | 2017184545 A1 | 10/2017 |

OTHER PUBLICATIONS

International Preliminary Report on Patentability for PCT/EP2019/063862 dated Dec. 10, 2020, 10 pages.
Wrigstedt et al., "Microwave-enhanced aqueous biphasic dehydration of carbohydrates to 5-hydroxymethylfurfural", RSC Advances, vol. 6, No. 23, 2016, pp. 18973-18979.
International Search Report and Written Opinion for PCT/EP2019/063862 dated Oct. 2, 2019, with English translation, 20 pages.
Gomes et al., "Going Beyond the Limits of the Biorenewable Platform: Sodium Dithionite-promoted Stabilization of 5-Hydroxymethylfurfural", CHEMSUSCHEM, vol. 11, No. 10, 2018, 28 pages.
Choudary et al., "Insights into the Interplay of Lewis and Bronstad Acid Catalysts in Glucose and Fructose Conversion in 5-(Hydroxymethyl)furfural and Levulinic Acid in Aqueous Media", Journal of the American Chemical Society, vol. 135, No. 10, 2013, pp. 3997-4006.
Van Dam et al., "The Conversion of Fructose and Glucose in Acidic Media: Formation of Hydroxymethylfurfural", Starch: International Journal for the Investigation: Processing and Use of Carbohydrates and Their Derivatives, DE, vol. 38, No. 3, 1986, pp. 95-101.

* cited by examiner

*Primary Examiner* — Golam M Shameem
(74) *Attorney, Agent, or Firm* — Sheppard Mullin Richter & Hampton LLP

(57) ABSTRACT

The present invention relates to a method for the production of 5-hydroxymethylfurfural (HMF), which converts a fructose-containing component using a catalyst system comprising a solution of a salt and acid mixture at a temperature of 90 to 200° C. and leads to obtaining an HMF-containing product mixture, wherein advantageously a high HMF selectivity with significantly lower by-product formation is achieved at the same time.

25 Claims, 13 Drawing Sheets

PREPARATION OF HMF CATALYZED BY A MIXTURE OF SALT AND ACID

CROSS-REFERENCE TO RELATED APPLICATIONS

This application is a U.S. National Stage Application under 35 U.S.C. § 371 of International Application No. PCT/EP2019/063862, filed May 28, 2019, which claims priority to DE 102018208510.2, filed May 29, 2018, the contents of which are incorporated to the present disclosure by reference.

The present invention relates to a method for the production of 5-hydroxymethylfurfural (HMF), which converts a fructose-containing component using a catalyst system comprising a solution of a salt and acid mixture at a temperature of 90 to 200° C. and for obtaining an HMF-containing product mixture, wherein advantageously a high HMF selectivity is achieved with significantly lower formation of byproducts.

5-Hydroxymethylfurfural (HMF) is a multifunctional molecule with an aromatic 5-ring system, an aldehyde group and an alcohol group. The many functionalities make the molecule a platform chemical that lends itself to many different applications and that can serve as the basis for a large number of other compounds. The compounds that can be produced on the basis of HMF firstly include chemicals such as caprolactam or adipic acid that are presently already being produced via bulk production using petrochemical methods, but also compounds such as 2,5-furandicarboxylic acid (FDCA), which can be used for a large range of applications, for which no technical production method is presently available.

Despite the great potential of HMF and FDCA, there has been a lack of economical, technically established production methods for these compounds. The multifunctionality of HMF as one of the greatest advantages of the molecule has also proven to be a major disadvantage in terms of its synthesis with regard to the secondary chemical processes which may subsequently occur as a result of this multifunctionality. Especially in aqueous systems, HMF is not stable under the reaction conditions necessary for the synthesis (acidic pH value, elevated temperature) and, firstly, HMF reacts under polymerization with itself and/or the starting materials and intermediate products to form so-called humins which are soluble or insoluble depending on the chain length and lead to a brown to black coloration of the reaction solution. Another undesirable secondary reaction is the acid-catalyzed rehydration of HMF to form levulinic and formic acid, wherein levulinic acid in particular can react with HMF to form further undesirable byproducts. For the most economical production of HMF it is therefore absolutely necessary to avoid the occurrence of this side reaction and the secondary reaction of HMF and levulinic acid as far as possible.

In principle, a distinction can be made between single-phase and two-phase reaction systems in the numerous different synthetic routes that have been described in the prior art for the production of HMF. Both approaches can use both homogeneous and heterogeneous catalysts. In the single-phase systems, the HMF synthesis can be carried out not only in purely aqueous systems but also in organic solvents, such as DMSO, DMF and sulfolane, or in ionic liquids. Avoiding aqueous systems leads to better selectivities for HMF purely in terms of the chemical reaction, but for removing the solvents, high temperatures are often necessary, at which the thermal decomposition of HMF can occur, which in turn significantly reduces the purity and yield of HMF. In addition, when using water-free systems, the costs for the solvents as well as safety and environmental aspects play a major role. It also proves to be disadvantageous that the hexoses used for HMF synthesis, in particular fructose and/or glucose, have poor solubility in many common organic solvents.

In the two-phase reaction systems, the reaction of hexose to form HMF is carried out in an aqueous phase and the resulting HMF is continuously extracted using an organic solvent. The solvent must not be miscible with water and must have a sufficiently high partition coefficient for HMF between the aqueous and organic phases in order to ensure efficient extraction of HMF. Since, in particular, the distribution coefficients for most solvents are not very high, very large amounts of solvent must often be used in such systems. The organic solvent most frequently used in two-phase reaction systems is methyl isobutyl ketone (MIBK), which is optionally used in combination with phase modifiers such as 2-butanol. As already shown for the single-phase anhydrous reaction systems, the subsequent removal of the solvent(s) used proves to be problematic because of the high boiling points of suitable solvents.

EP 0 230 250 B1 discloses a method for the production of 5-hydroxymethylfurfural including a crystalline product using only water as solvent. In the batch method described, saccharides are decomposed in aqueous solution at a temperature of over 100° C. with an acidic catalyst to a mixture of hexoses and HMF and subsequently, the formed HMF is separated over ion exchange columns at a temperature of 35 to 85° C. from byproducts, so that in addition to an HMF fraction, a saccharide fraction can be obtained which is available for another HMF synthesis according to the method described. The batchwise conversion disclosed in this document entails a high fructose conversion and as a direct result a high HMF concentration in the reaction solution which, under the prevailing conditions, leads to an increased formation of byproducts and degradation products, whereby the HMF yield is reduced in relation to the converted amount of fructose.

WO 2013/106136 A1 relates to a method for the production of HMF and HMF derivatives from sugar, comprising the recovery of unreacted sugars which are suitable for direct use in ethanol fermentation. Hexose-containing solutions in the aqueous phase are converted into HMF by an acid-catalyzed dehydration reaction, subsequently the unreacted sugars contained in the product mixture are separated from the product mixture by adsorption and/or solvent extraction and these are finally used in aerobic or anaerobic fermentation processes to produce ethanol. It is taught to carry out the acid catalyzed dehydration reaction at a temperature of 175 to 205° C.

WO 2015/113060 A2 discloses the conversion of fructose-containing starting materials to HMF-containing products. By means of the method described, fructose, water, an acid catalyst and at least one other solvent are mixed in a reaction zone and, by choosing suitable reaction parameters, reacted for a period of about 1 to 60 minutes, so that an HMF yield of 80% is not exceeded. When the specified conversion is completed, the reaction components are immediately cooled in order to minimize the formation of undesired byproducts.

WO 2014/158554 discloses a method for the production of HMF or derivatives thereof from solutions containing glucose and/or fructose, wherein the acid-catalyzed dehydration reaction is carried out under oxygen-reduced conditions. This should increase the stability of HMF and prevent possible degradation reactions so that the formation of undesired byproducts is reduced. Optionally, antioxidants are added in order to prevent an auto-oxidation reaction of HMF.

Li et al. (RSC Adv., 2017, 7, 14330-14336) describe the conversion of glucose to HMF without isomerization to fructose using a mixture of hydrochloric acid and sodium chloride in a water/γ-valerolactone system at a temperature of 140° C. and a reaction time of 60 min. As already mentioned above, however, the final removal of the solvent is also problematic here due to the high boiling point of 205° C., since the decomposition of HMF already occurs from a temperature of 170° C. onwards.

To ensure a cost-effective and effective production method for HMF, it is crucial that during the conversion of a fructose-containing starting solution to HMF, the formation of undesired byproducts and the decomposition of HMF formed by the dehydration reaction are avoided as far as possible by choosing suitable reaction conditions and method steps. Furthermore, it makes economic sense if the unconverted fructose is separated from the disruptive byproducts formed during the dehydration reaction and is thus made available in as pure a form as possible for recycling to the continuous production process.

A corresponding method for the cost-effective and effective production of HMF, preferably in a continuous process, is not known from prior art to date.

It is therefore the object of the present invention to overcome the mentioned disadvantages and limitations of the methods known from prior art, in particular to provide a method for converting fructose to HMF in a highly selective manner, in particular with maximum avoidance of byproduct formation and in a cost-effective and effective manner.

The object of the present invention is achieved by the technical teaching of the claims.

In particular, the present invention relates to a method for the production of 5-hydroxymethylfurfural (HMF) comprising the following steps:

a) providing a fructose-containing component and a catalyst system comprising a solution of a salt and acid mixture, b) mixing the fructose-containing component with the catalyst system to obtain a reaction solution, c) converting the fructose present in the reaction solution to HMF at a temperature of 90° C. to 200° C. to obtain a liquid HMF-containing product mixture and d) obtaining a liquid HMF-containing product mixture.

According to the invention, a method is accordingly provided which produces 5-hydroxymethylfurfural (HMF) by selective, preferably highly selective, conversion of the fructose of a fructose-containing component. According to the invention, a catalyst system comprising a solution, in particular an aqueous solution, of a salt and acid mixture is used for converting the fructose. The present invention therefore advantageously provides for a fructose-containing component to be mixed with a solution, in particular an aqueous solution, a salt and acid mixture, and for the fructose present in the reaction solution to be subsequently converted to HMF. The use of a salt and acid mixture for converting the fructose present in the fructose-containing component into HMF is advantageous in that a significantly higher HMF selectivity is achieved compared to conventional HMF production methods, which use sulfuric acid as a catalyst, while at the same time the formation of byproducts is significantly reduced and fructose is converted at comparable rates. In an advantageous preferred embodiment, fructose conversions ≥30% with an acceptable selectivity of more than 80% are possible. In addition, the use of the salt and acid mixture also enables a higher carbohydrate concentration in the reaction solution, namely up to 40% dry matter carbohydrate in an advantageous preferred embodiment. According to the invention, the use of the catalyst system comprising a solution of a salt and acid mixture leads to very high HMF selectivities without the need to use other catalysts in homogeneous or heterogeneous form in an advantageous preferred embodiment. In addition, the use of the catalyst system according to the invention leads to a markedly lower formation of humic substances, in particular insoluble humic substances, which in the conventional process lead to technical problems due to caking and incrustations. The use of the salt and acid mixture according to the invention, i.e. of the catalyst system, accordingly leads in particular to significantly higher fructose conversions with an economically sensible HMF selectivity.

In a particularly preferred embodiment, the procedure according to the invention, in particular the implementation of method steps a) to d), enables significantly higher HMF selectivity to be achieved, wherein a reduced byproduct formation, in particular a reduced rehydration of HMF to levulinic acid and formic acid, occurs for comparable fructose conversions compared to prior art.

In a particularly preferred embodiment, the selectivity for levulinic acid in the method according to the invention, in particular method steps a) to d), is ≤6%, preferably ≤5%, preferably ≤4%, particularly preferably ≤3% (based on the content of converted fructose).

The catalyst system according to the invention comprises a solution of a salt and acid mixture, wherein the acid preferably is a mineral acid and/or an organic acid and the salt preferably is a salt of a mineral acid and/or an organic acid.

In a particularly preferred embodiment, the catalyst system according to the invention comprises a solution of a salt and acid mixture, wherein the acid preferably is a mineral acid, an organic acid or a mixture of a mineral acid and an organic acid.

In a particularly preferred embodiment, the catalyst system according to the invention comprises a solution of a salt and acid mixture, wherein the salt preferably is a salt of a mineral acid, a salt of an organic acid or a mixture of salts of a mineral acid and an organic acid.

The mineral acid is particularly preferably selected from the group consisting of hydrochloric acid, sulfuric acid, nitric acid and phosphoric acid; and the organic acid selected from the group consisting of acetic acid, citric acid, tartaric acid, oxalic acid, glycolic acid and gluconic acid. The salt of a mineral acid is particularly preferably selected from the group consisting of alkaline halides, alkaline earth halides, alkaline nitrates, alkaline earth nitrates, alkaline sulfates, alkaline earth sulfates, alkaline phosphates, alkaline earth phosphates and mixtures thereof; and the salt of an organic acid selected from the group consisting of acetates, citrates, tartrates, oxalates, glycolates, gluconates, and mixtures thereof.

In a preferred embodiment, the acid contained in the catalyst system according to the invention is a mineral acid. The mineral acid is particularly preferably selected from the group consisting of hydrochloric acid, sulfuric acid, nitric acid and phosphoric acid. The mineral acid is particularly preferably hydrochloric acid or nitric acid. In a further preferred embodiment, the acid contained in the catalyst system is an organic acid. The organic acid is particularly preferably selected from the group consisting of acetic acid, citric acid, tartaric acid, oxalic acid, glycolic acid and gluconic acid.

In a preferred embodiment, the salt contained in the catalyst system according to the invention is a salt of a mineral acid. The salt is particularly preferably selected from the group consisting of alkaline halides, alkaline earth halides, alkaline nitrates, alkaline earth nitrates, alkaline sulfates, alkaline earth sulfates, alkaline phosphates, alkaline earth phosphates and mixtures thereof. The salt sodium chloride, sodium nitrate, calcium chloride, magnesium chloride or mixtures thereof is particularly preferred. In a further preferred embodiment, the salt contained in the catalyst system is a salt of an organic acid. The salt is particularly preferably selected from the group consisting of acetates, citrates, tartrates, oxalates, glycolates, gluconates and mixtures thereof.

In a particularly preferred embodiment, the solution of a salt and acid mixture is an aqueous solution. According to the invention, a single-phase procedure is preferably provided. A two-phase procedure is preferably excluded. Preferably, no phase separation, in particular no induced phase separation, is provided. The catalyst system according to the invention comprises, in particular consists of, an aqueous solution of a salt and acid mixture, wherein the acid is a mineral acid, preferably selected from the group consisting of hydrochloric acid, sulfuric acid, nitric acid and phosphoric acid and the salt is a salt of a mineral acid, preferably selected from the group consisting of sodium chloride, sodium nitrate, calcium chloride and magnesium chloride.

In a particularly preferred embodiment, the catalyst system according to the invention comprises sodium chloride as the salt and hydrochloric acid as the mineral acid.

In a further preferred embodiment, the catalyst system according to the invention comprises sodium nitrate as the salt and nitric acid as the mineral acid.

In a further preferred embodiment of the present invention, the catalyst system according to the invention comprises hydrochloric acid as the mineral acid and calcium chloride as the salt.

In a further preferred embodiment of the present invention, the catalyst system according to the invention comprises hydrochloric acid as the mineral acid and magnesium chloride as the salt.

In a further preferred embodiment, the salt is an alkaline or alkaline earth salt, in particular an alkaline salt, in particular an alkaline earth salt.

Surprisingly, with a mixture of nitric acid and sodium nitrate as the catalyst system in the method according to the invention, good results with regard to HMF selectivity were achieved, although nitrates were previously considered to be an unsuitable catalyst for the formation of HMF (see Examples 4 and 6; Tao et al., Journal of Molecular Catalysis A: Chemical, 357, 2012, 11-18; Tyrlik et al., Starch/Strength, 47 (5), 1995, 171-174).

In a further embodiment, the catalyst system comprises, in particular consists of, an aqueous solution of a salt and acid mixture, wherein the acid is an organic acid, preferably selected from the group consisting of acetic acid, citric acid, tartaric acid, oxalic acid, glycolic acid and gluconic acid, and the salt is a salt of an organic acid, preferably selected from the group consisting of acetates, citrates, tartrates, oxalates, glycolates and gluconates.

The concentration of the salt and acid mixture, i.e., the catalyst system, in the method according to the invention is preferably 0.01 to 2.00 wt.-%, preferably 0.05 to 1.75 wt.-%, preferably 0.1 to 1.5 wt.-%, preferably 0.2 to 1.4 wt.-%, preferably 0.3 to 1.3 wt.-%, preferably 0.4 to 1.2 wt.-%, preferably 0.5 to 1.1 wt.-%, preferably 0.6 to 1.0 wt.-%, preferably 0.75 to 0.9 wt.-%, (in each case based on the total weight of the reaction solution obtained in method step b)). The catalyst system is preferably used in a concentration of at most 2.0 wt.-%, preferably at most 1.75 wt.-%, preferably at most 1.5 wt.-%, preferably at most 1.3 wt.-%, preferably at most 1.0 wt.-%, preferably at most 0.75 wt.-%, preferably at most 0.5 wt.-% (based in each case on the total weight of the reaction solution obtained in method step b)). These concentrations are well below the concentrations used in prior art. Surprisingly, however, it is precisely for these low concentrations of the salt and acid mixture that a particularly high HMF selectivity results in combination with a low formation of byproducts.

In a preferred embodiment, the salt concentration of the reaction solution in method step b) of the method according to the invention is $1\times10^{-5}$ to 0.45 mol/L, preferably $5\times10^{-5}$ to 0.4 mol/L, preferably $1\times10^{-4}$ to 0.35 mol/L, preferably $1\times10^{-3}$ to 0.3 mol/L, particularly preferably 0.01 to 0.25 mol/L.

In a preferred embodiment, the acid concentration of the reaction solution in method step b) of the method according to the invention is $1\times10^{-6}$ to 0.35 mol/L, preferably $8\times10^{-6}$ to 0.3 mol/L, preferably $1\times10^{-5}$ to 0.25 mol/L, preferably $1\times10^{-4}$ to 0.2 mol/L, particularly preferably $1\times10^{-3}$ to 0.15 mol/L.

Within the catalyst system according to the invention, the ratio of salt to free acid in the reaction solution obtained in method step b) is 0.8 to 10, preferably 1 to 9, preferably 1.2 to 8, preferably 1.5 to 7, preferably 2 to 6, preferably 2.3 to 5, preferably 2.5 to 4 (in each case mol/mol).

The ratio of anions of the salt and acid mixture to cations of the salt of the salt and acid mixture in the reaction solution obtained in method step b) is particularly preferably 0.55 to 4, preferably 1.0 to 3.5, preferably 1.1 to 2.0, preferably 1.5 to 3, preferably 1.75 to 2.75, preferably 2 to 2.5 (in each case mol/mol).

According to the invention, the concentration of anions of the catalyst system in the reaction solution obtained in method step b) is $1\times10^{-5}$ to 0.6 mol/L, preferably $8\times10^{-5}$ to 0.55 mol/L, preferably $1\times10^{-4}$ to 0.53 mol/L, preferably $1\times10^{-3}$ to 0.45 mol/L, preferably 0.01 to 0.35 mol/L, preferably 0.05 to 0.5 mol/L, preferably 0.1 to 0.4 mol/L, preferably 0.2 to 0.3 mol/L.

According to the invention, the concentration of cations of the catalyst system in the reaction solution obtained in method step b) is $1\times10^{-5}$ to 0.45 mol/L, preferably $5\times10^{-5}$ to 0.4 mol/L, preferably $1\times10^{-4}$ to 0.35 mol/L, preferably $1\times10^{-3}$ to 0.3 mol/L, particularly preferably 0.01 to 0.25 mol/L.

The use of the catalyst system according to the invention in the above-mentioned preferred concentrations preferably leads to a pH of the reaction solution obtained in method step b) of 1.2 to 4.5, preferably 1.3 to 4, preferably 1.4 to 3.5, preferably 1.5 to 3, preferably 1.7 to 2.5, preferably 2 to 2.2. The pH of the reaction solution obtained in step b) is thus mostly higher than in purely acid-catalyzed processes due to the use of the salt in the catalyst system according to the invention, but as a result surprisingly a higher HMF selectivity can be achieved (see examples).

In the method according to the invention, in particular in method steps a) to d), in particular a) to c), apart from the salt and acid mixture, no further catalytically active component is preferably used.

In a particularly preferred embodiment it is provided that in the method according to the invention, in particular in method steps a) to d), in particular a) to c), no organic solvent is used. In particular, in method steps a) to d), in particular a) to c), no organic solvent is used which is miscible with water or immiscible with water.

In particular, method steps a) to d) occur in aqueous solution.

In addition to the salt and acid mixture, a fructose-containing component is provided in step a) of the method according to the invention. This is preferably a solid fructose-containing component, in particular fructose, or a liquid fructose-containing component, in particular a fructose syrup, a fructose/glucose syrup or a fructose solution, in particular an aqueous fructose solution. The fructose-containing component is therefore also referred to here as the fructose-containing starting solution. According to the invention, the fructose-containing component can also be obtained from sucrose or starch, or glucose obtained from biomass can be isomerized to fructose. The fructose-containing component preferably has a dry matter content (DM) of 40 to 100 wt.-%, preferably 50 to 90 wt.-%, preferably 60 to 85 wt.-% of fructose.

In a preferred embodiment of the present invention, the components provided in step a) are mixed in step b) to obtain a reaction solution with a carbohydrate content of 5 wt-% to 50 wt.-% (dry matter, hereinafter also DM, carbohydrate in relation to total weight of reaction solution) and converted according to method step c). The carbohydrate content of the reaction solution in step b) is particularly preferably 10 wt.-% to 45 wt.-%, preferably 15 wt.-% to 40 wt.-%, preferably 25 wt.-% to 35 wt.-%, preferably 20 wt.-%, 30 wt.-% or 40 wt.-% (in each case DM carbohydrate in relation to the total weight of the reaction solution).

In a preferred embodiment of the present method, the fructose content of the reaction solution obtained in method step b) is 40 wt.-% to 100 wt.-%, preferably 70 wt.-% to 100 wt.-%, preferably 80 wt.-% to 100 wt.-%, preferably 90 wt.-% to 100 wt.-%, preferably 95 wt.-% to 100 wt.-%, preferably 40 wt.-% to 99 wt.-%, preferably 45 wt.-% to 99 wt.-% -%, preferably 50 wt.-% to 95 wt.-%, preferably 45 wt.-% to 90 wt.-%, preferably 55 wt.-% to 85 wt.-% (in each case DM fructose in relation to the dry matter of the carbohydrate content, i.e., all the carbohydrates present in the reaction solution).

In a particularly preferred embodiment of the present invention, the components provided in step a) are mixed in step b) to obtain a reaction solution with a carbohydrate content of 5 wt.-% to 50 wt.-%, preferably 10 wt.-% to 45 wt.-%, preferably 15 wt.-% to 40 wt.-%, preferably 25 wt.-% to 35 wt.-%, preferably 20 wt.-%, 30 wt.-% or 40 wt.-%, (each DM carbohydrate in relation to the total weight of the reaction solution) and a fructose content of 40 wt.-% to 100 wt.-%, preferably 70 wt.-% to 100 wt.-%, preferably 80 wt.-% to 100 wt.-%, preferably 90 wt.-% to 100 wt.-%, preferably 95 wt.-% to 100 wt.-%, preferably 40 wt.-% to 99 wt.-%, preferably 45 wt.-% to 99 wt.-%, preferably 50 wt.-% to 95 wt.-%, preferably 45 wt.-% to 90 wt.-%, preferably 55 wt.-% to 85 wt.-% (in each case DM fructose in relation to the dry matter of the carbohydrate content, i.e., all carbohydrates present in the reaction solution) and converted according to method step c).

In a particularly preferred embodiment, the mixing, i.e., step b) of the method according to the invention, of the components used to prepare the reaction solution, i.e., in particular the fructose-containing component and the catalyst system, occurs in a mixing device and/or a conduit. The mixing device or the conduit and the reactor system in which the conversion, i.e., step c) of the present method occurs, can represent spatially separate structural units that are connected to one another by at least one conduit; they can also represent separate but integral components of a device. The reaction solution is preferably introduced into the reactor system with the aid of a pump, in particular a high pressure pump.

In a preferred embodiment of the present invention, the fructose-containing component provided in step a), the catalyst system or both is set to a temperature of 90° C. to 200° C. before step b). Before step b) preferably at least one, preferably all of the components provided in step a), i.e., the fructose-containing component and the catalyst system, are preheated separately from one another to a temperature of 90° C. to 200° C., preferably 100° C. to 175° C., preferably 150° C. to 175° C. In a preferred embodiment of the present invention, at least one, preferably all of the components provided in step a) are preheated to a temperature of 120° C. to 180° C., preferably 130° C. to 180° C., preferably 140° C. to 180° C. before step b). In particular, before step b) at least one, preferably all of the components provided in step a) are preheated separately from one another to a temperature of 160° C., 165° C., 170° C. or 175° C.

In an alternative preferred embodiment of the present invention, the reaction solution obtained in step b) is set to a temperature of 90° C. to 200° C. Preference is therefore given to the reaction solution obtained in step b) by mixing the components provided in step a), preferably after step b) and before step c), to a temperature of 90° C. to 200° C., preferably 100° C. to 175° C., preferably 150° C. to 175° C. The reaction solution obtained in step b), preferably after step b) and before step c), is preferably heated to a temperature of 120° C. to 180° C., preferably 130° C. to 180° C., preferably 140° C. to 180° C. In particular, the reaction solution obtained in step b) is heated to a temperature of 160° C., 165° C., 170° C. or 175° C.

In a particularly preferred embodiment, the subsequent step c) of the present method, i.e., the conversion of the fructose present in the reaction solution to HMF, is carried out at a temperature of 90 to 200° C., in particular 120 to 195° C., in particular 140 to 190° C., in particular 150 to 180° C., in particular 160 to 175° C., in particular 165 to 170° C., in particular 165 to 175° C., in particular 170 to 175° C., in particular 160 to 165° C., in particular 165° C., in particular 170° C., in particular 175° C.

According to the invention, at any point in time the temperature used to carry out the method according to the invention is, in a preferred embodiment, at most 200° C., preferably at most 175° C., in particular at most 165° C.

In a preferred embodiment of the present invention, the fructose contained in the reaction solution is converted to HMF in step c) in a period of 0.1 to 20 min., in particular 0.1 to 15 min., in particular 8 to 13 min., in particular 4 to 10 min., in particular 8 to 10 min., preferably 0.1 to 8 min., preferably 0.2 to 7 min., preferably 0.5 to 5 min., preferably 1 to 4 min., preferably 5 to 6 min. The fructose is preferably converted to HMF in step c) in a period of at most 10 min., preferably at most 9 min., preferably at most 8 min., preferably at most 7 min., preferably at most 6 min., preferably at most 5 min., preferably at most 4 min.

In a preferred embodiment, the invention provides that a fructose conversion of 1 mol-% to 50 mol-% is achieved in step c). In a preferred embodiment, the fructose is converted to HMF in step c) with a fructose conversion of 1 mol-% to 50 mol-%, preferably 5 mol-% to 40 mol-%, preferably 10 mol-% to 30 mol-% mol-%, preferably 15 mol-% to 2.5 mol-%, preferably 20 mol-% to 25 mol-%. The fructose is preferably converted to HMF in step c) with a fructose conversion of at most 50 mol-%, preferably at most 40 mol-%, preferably at most 30 mol-%, preferably at most 25 mol-%, preferably at most 20 mol-%. According to the invention, this occurs at a temperature of 90° C. to 200° C.

In connection with the present invention, "setting a fructose conversion" means that the reaction parameters used for the conversion of fructose to HMF, in particular the reaction temperature and the reaction time in the reactor, are chosen so that there is only a limited conversion of the fructose from a maximum of 50 mol-%, whereby a high HMF selectivity and at the same time a low byproduct formation can be achieved.

It is therefore preferably possible to provide specifically defined fructose conversions within the framework of the given parameters, particular by using the reaction temperature preferred according to the invention, optionally also the reaction time in a preferred embodiment, for step c). An HMF selectivity which is preferred according to the invention can also be set on the basis of these parameters. In a preferred manner according to the invention, the desired fructose conversion and, optionally, the HMF selectivity can be set by taking a sample during the process, analyzing the sample and then calculating the parameters to be maintained or set to achieve the desired fructose conversion values and the optionally desired HMF selectivity.

In a particularly preferred embodiment, the fructose contained in the fructose-containing component is converted in step c) at a temperature of 90 to 200° C., preferably 150 to 190° C., in particular 160° C., 165° C., 170° C. or 175° C. for a period of 4 to 7 min., preferably 5 to 6 min., in particular 5.6 min. This preferably leads to a fructose conversion of 1 to 50 mol-%.

In a preferred embodiment of the present invention, the method is set so that in step c) an HMF selectivity of 60 mol-% to 100 mol-%, preferably 65 mol-% to 100 mol-%, preferably 70 mol-% to 100 mol-%, preferably 75 mol-% to 100 mol-%, preferably 80 mol-% to 100 mol-%, preferably 85 mol-% to 100 mol-%, preferably 90 mol-% to 100 mol-% is obtained. The HMF selectivity in step c) is preferably at least 60 mol-%, preferably at least 65 mol-%, preferably at least 70 mol-%, preferably at least 75 mol-%, preferably at least 80 mol-%, preferably at least 85 mol-%, preferably at least 90 mol-%, preferably at least 95 mol-%.

In a preferred embodiment of the present invention, the method is set so that in step c) an HMF selectivity of 60 mol-% to 100 mol-%, preferably 65 mol-% to 100 mol-%, preferably 70 mol-% to 100 mol-%, preferably 75 mol-% to 100 mol-%, preferably 80 mol-% to 100 mol-%, preferably 85 mol-% to 100 mol-%, preferably 90 mol-% to 100 mol-%, preferably at least 60 mol-%, preferably at least 65 mol-%, preferably at least 70 mol-%, preferably at least 75 mol-%, preferably at least 80 mol-%, preferably at least 85 mol-%, preferably at least 90 mol-%, preferably at least 95 mol-% and a fructose conversion of 1 mol-% to 50 mol-%, preferably 5 mol-% to 40 mol-%, preferably 10 mol-% to 30 mol-%, preferably 15 mol-% to 25 mol-%, preferably 20 mol-% to 25 mol-%, preferably at most 50 mol-%, preferably at most 40 mol-%, preferably at most 30 mol-%, preferably at most 25 mol-%, preferably at most 20 mol-% is obtained.

In a particularly preferred embodiment of the present invention, the method is set so that in step c) an HMF selectivity of 60 mol-% to 100 mol-%, preferably 65 mol-% to 100 mol-%, preferably 70 mol-% to 100 mol-%, preferably 75 mol-% to 100 mol-%, preferably 80 mol-% to 100 mol-%, preferably 85 mol-% to 100 mol-%, preferably 90 mol-% to 100 mol-%, preferably at least 60 mol-%, preferably at least 65 mol-%, preferably at least 70 mol-%, preferably at least 75 mol-%, preferably at least 80 mol-%, preferably at least 85 mol-%, preferably at least 90 mol-%, preferably at least 95 mol-% and a fructose conversion of 1 mol-% to 50 mol-%, preferably 5 mol-% to 40 mol-%, preferably 10 mol-% to 30 mol-%, preferably 15 mol-% to 25 mol-%, preferably 20 mol-% to 25 mol-%, preferably at most 50 mol-%, preferably at most 40 mol-%, preferably at most 30 mol-%, preferably at most 25 mol-%, preferably at most 20 mol-% is obtained, wherein this is achieved using a temperature of 90 to 200° C., in particular 140 to 190° C., in particular 150 to 180° C., in particular 160 to 175° C., in particular 165 to 170° C., in particular 165 to 175° C., in particular 170 to 175° C., in particular 160 to 165° C., in particular 165° C., in particular 170° C., in particular 175° C. and within a period of 0.1 to 20 min, in particular 0.1 to 15 min, in particular 8 to 13 min, in particular 4 to 10 min., in particular 8 to 10 min., preferably 0.1 to 8 min., preferably 0.2 to 7 min., preferably 0.5 to 5 min., preferably 1 to 4 min., preferably 5 to 6 min.

In connection with the present invention, the HMF selectivity is related to the converted fructose content, wherein contents of other carbohydrates, in particular glucose, are not taken into account.

In a preferred embodiment of the present invention, the HMF yield is 3 to 50 mol-%, preferably 5 to 45 mol-%, preferably 10 to 40 mol-%, preferably 15 to 35 mol-%, particularly preferably 20 to 30 mol-%.

In a preferred embodiment of the present invention, in step c) the pressure for converting the fructose present in the reaction solution to HMF is set such that boiling of the reaction solution and thus the occurrence of vapor bubbles is avoided. The pressure for converting the fructose present in the reaction solution to HMF in the reactor system is preferably 0.1 to 2 MPa, preferably 0.2 to 1.5 MPa, particularly preferably 1 MPa.

According to the invention it is provided that the fructose present in the reaction solution is converted to HMF in step c) by setting various parameters such as temperature, reaction time, pH, catalyst concentration, acid/salt ratio and/or pressure, and in step d) a liquid HMF-containing product mixture is obtained. The method is therefore preferably carried out in such a way that by setting the temperature, and preferably also the reaction time, there is a targeted limited conversion of the fructose of 1 mol-% to 50 mol-%, whereby a surprisingly high HMF selectivity, preferably of 60 mol-% to 100 mol-%, can be achieved.

In a particularly preferred embodiment, conversion of fructose present in the reaction solution to HMF and obtaining HMF according to method steps c) and d) provides a one-step method. In particular, the procedure according to the invention according to method steps c) and d) is preferably not a two-stage procedure.

In a preferred embodiment, the present method further comprises the following step:

e) cooling the liquid HMF product mixture obtained in step d) to a temperature of 20° C. to 80° C., preferably 25° C. to 70° C., preferably 30° C. to 60° C., preferably 30° C. to 55° C., preferably 30° C. to 50° C., preferably 30° C. to 45° C., preferably 30° C. to 40° C., preferably 80° C., preferably 70° C., preferably 60° C., preferably 55° C., preferably 50° C., preferably 45° C., preferably 40° C., preferably 35° C., preferably 30° C. The liquid HMF product mixture in step e) is preferably cooled to a temperature of at most 75° C., preferably at most 70° C., preferably at most 60° C., preferably at most 55° C., preferably at most 50° C., preferably at most 45° C., preferably at most 40° C., preferably at most 35° C. According to the invention, this can be done in one or two stages.

In a preferred embodiment of the present invention, the temperature of the liquid HMF product mixture in step e) is set or cooled in a period of 0.1 to 10 min., preferably 0.1 to 9 min., preferably 0.1 to 8 min., preferably 0.2 to 7 min., preferably 0.2 to 6 min., preferably 0.5 to 5 min., preferably 0.5 to 4 min., preferably 0.5 to 3 min. The temperature of the product mixture in step e) is set or cooled preferably in at most 10 min., preferably at most 9 min., preferably at most 8 min., preferably at most 7 min., preferably at most 6 min., preferably at most 5 min., preferably at most 4 min , preferably at most 3 min., preferably at most 2 min, preferably at most 1 min, preferably at most 0.5 min.

Thus, the HMF-containing product mixture obtained in step d) is cooled to a temperature of 20° C. to 80° C. after reaching the limited fructose conversion of a maximum of 50 mol-% in step e). This advantageously largely prevents the formation of undesired byproducts and the decomposition of the HMF formed.

The method according to the invention for the production of HMF is preferably carried out in a suitable reactor system. According to the invention, this is preferably a continuous reactor system.

In a particularly preferred embodiment, the continuous reactor system used is designed as a tubular reactor system. Such a continuous reactor system is a reactor system known to the person skilled in the art. In a particularly preferred embodiment, a continuous reactor system, in particular a continuous system, with little backmixing can also be used. In a particularly preferred embodiment, a plug-flow reactor (PFR) can be used as the continuous reactor system. In a preferred embodiment, the continuous reactor system can also be designed as a flow tube, stirred kettle or stirred kettle cascade. In connection with the present invention, a plug-flow reactor (PFR) is understood to mean a so-called ideal flow tube [in German: "ideales Strömungsrohr, IR"], i.e. a tubular reactor in which there is a plug flow. A reactor of this type also distinguished in particular by the fact that there is no mixing, backflow or turbulence of the reaction solution carried out, but rather a uniform flow occurs with material conversion occuring in parallel. The plug-flow reactor ensures, in particular, that each substance fed into the plug-flow reactor, in particular each component fed in, is continuously converted under the same conditions, i.e. all components are exposed to the conversion process for the same period of time.

In a preferred embodiment, the present method optionally further comprises the following step:
  f) filtration, decolorization and/or purification of the liquid HMF product mixture.

That means, in a further preferred embodiment, the HMF product mixture is filtered, preferably using a suitable filter or a suitable filter system, and the product mixture is decolorized and/or purified, preferably decolorized and/or purified using activated carbon. The product mixture is preferably filtered using a suitable filter or a suitable filter system and the product mixture is decolorized and/or purified, using for example activated carbon, after step e). The product mixture is preferably filtered using a suitable filter or a suitable filter system and the product mixture is decolorized and/or purified, for example using activated carbon, before step g) or h). In a particularly preferred embodiment, after method step e) and/or method step g), the product mixture can be filtered using a suitable filter or a suitable filter system, it can be decolorized and/or purified in any order, in particular using activated carbon and, optionally, after step g) another filtration using a suitable filter or a suitable filter system can be carried out. In a particularly preferred embodiment, after step e) and/or method step g), firstly a filtration using a suitable filter or a suitable filter system and subsequently a decolorization and/or purification, in particular using activated carbon and, optionally after step g), another filtration using a suitable filter or a suitable filter system in this order is carried out. According to the invention, a sintered metal filter is preferably used for the filtration.

Preferably, by filtering the product mixture over a suitable filter or a suitable filter system and decolorizing and/or purifying it over, for example, activated carbon, undesired byproducts, in particular soluble and insoluble humic substances, are removed from the product mixture.

In a preferred embodiment of the present invention, the product mixture obtained in step e) or optionally step f) has a dry matter content of 5 to 50 wt.-%, preferably 10 to 40 wt.-%, preferably at least 5 wt.-%, preferably at least 10 wt.-%, preferably at most 40 wt.-%, preferably at most 60 wt.-%.

If the dry matter content of the product mixture obtained in step e) or, optionally, f) is too low, the invention can provide that the present method optionally further comprises the following step:
  g) setting the liquid HMF product mixture to a dry matter content of 20 to 70 wt.-%, preferably 25 to 50 wt.-%, preferably 25 to 45 wt.-%, preferably 30 to 45 wt.-%, preferably 30 to 40 wt.-%.

In a further preferred embodiment, the product mixture obtained in step e) or optionally f) is reduced to a dry matter content of 20 to 70 wt.-%, preferably at least 20 wt.-%, preferably at least 30 wt.-%, preferably at least 40 wt.-%, preferably at least 50 wt.-%, preferably at most 70 wt.-%, preferably at most 60 wt.-%, preferably at most 50 wt.-%.

In a preferred embodiment, the present method further comprises the following steps:
  h) purification of the liquid HMF product mixture by means of chromatography, ultra- and/or nanofiltration, extraction with a suitable extractant, adsorption on a suitable material and subsequent targeted desorption and/or electrodialysis to separate at least one HMF fraction, and
  i) obtaining at least one HMF fraction.

That is to say, at least one HMF fraction is preferably separated from the liquid HMF-containing product mixture by using at least one of the above-mentioned purification processes, so that only other components contained in the product mixture such as unreacted fructose, glucose or byproducts such as organic acids and humins remain. It can also be provided according to the invention to use a combination of at least two or more of the purification processes mentioned for the separation of at least one HMF fraction and/or optionally other fractions containing one or more other components of the product mixture.

In an alternative preferred embodiment, the present method further comprises the following steps:
  h) purification of the liquid HMF product mixture by means of chromatography, ultra- and/or nanofiltration, extraction with a suitable extractant, adsorption on a suitable material and subsequent targeted desorption and/or electrodialysis to separate at least one fraction selected from the group consisting of an HMF fraction, a glucose fraction, a fructose fraction and an organic acid fraction, and i) obtaining at least one fraction selected from the group consisting of an HMF fraction, a glucose fraction, a fructose fraction and an organic acid fraction.

It can further be provided that at least one of the fractions obtained in step i) is further processed using a purification process selected from the group consisting of chromatography, ultra- and/or nanofiltration, extraction with a suitable extractant, adsorption on a suitable material and subsequent targeted desorption and/or electrodialysis.

One of the purification processes provided in the method according to the invention is ultra- and/or nanofiltration. Suitable membranes can be used to firstly concentrate the liquid HMF-containing product mixture, but secondly to remove soluble and/or insoluble humins or, in the case of nanofiltration, to separate HMF and/or organic acids from the product mixture. Preferably, a concentrated product mixture, a product mixture freed from soluble and/or insoluble humic substances, an HMF fraction and a product mixture freed from HMF, an HMF fraction and/or an organic acids fraction and a product mixture freed from HMF and/or organic acids, or a glucose and/or fructose fraction and a product mixture freed from humins and/or glucose and/or fructose can be obtained by ultra and/or nano filtration.

Another purification process provided in the method according to the invention is extraction with a suitable extraction agent. To extract HMF from the HMF-containing product mixture, a solvent is preferably used which is immiscible or hardly miscible with water and which has a sufficiently high affinity for HMF. Ideally, the boiling point of the organic solvent is preferably relatively low and the density difference between water and the solvent is sufficiently high so that phase separation can be achieved. Suitable solvents are preferably methyl isobutyl ketone, ethyl acetate, methyl ethyl ketone, butanol, diethyl ether, methyl butyl ether, isoamyl alcohol, methyl tetrahydrofuran or the like. After the extraction step, an aqueous product mixture which contains unreacted fructose and glucose remains, and an organic phase that contains HMF and possibly organic acids is obtained.

Another purification process provided in the method according to the invention is the adsorption onto a suitable material and the subsequent desorption. In principle, HMF can be adsorbed on any material that preferentially adsorbs HMF from hexose-containing solutions. Preferred materials are polymer-based resins such as divinylbenzene-styrene copolymers, adsorber resins, activated carbon, zeolites, aluminum oxides, non-functionalized resins or cation exchange resins. The product mixture obtained in step e), f) or g) is preferably brought into contact continuously with the HMF-adsorbing material, but at most until the material is exhausted. The adsorbed HMF is then desorbed with a suitable desorbent such as water or polar organic solvents such as alcohols, ethyl acetate, THF or the like. HMF can then be obtained from the organic solvent by suitable methods.

Another purification process provided in the method according to the invention is electrodialysis. This is an electrochemically driven membrane process in which ion exchange membranes are used in combination with an electrical potential difference to separate ionic species from uncharged species or impurities in the solution. In the case of the present method, electrodialysis can be used to free the product mixture from inorganic and/or organic cations and anions, such as salts front the salt and acid mixture, levulinic and formic acid as byproducts.

Another purification process provided in the method according to the invention is chromatography. This is explained in more detail below.

All of the above-mentioned purification processes can be used individually or in combination with one another.

In step h), HMF contained in the product mixture is particularly preferably separated from the other components of the product mixture using a chromatographic method, in particular by means of chromatography on ion exchange resins, in particular cation exchange resins, in particular by means of single or multi-stage chromatography on ion exchange resins, in particular cation exchange resins.

In a particularly preferred embodiment of the present invention, the chromatography, in particular chromatography on ion exchange resins, in particular chromatography on cation exchange resins, is ion exchange chromatography, in particular cation exchange chromatography.

In a preferred embodiment of the present invention, the liquid HMF product mixture is separated in step h) by means of chromatography into at least four fractions, comprising an HMF fraction, a glucose fraction, a fructose fraction and an organic acid fraction, and in step i) at least one HMF fraction, a glucose fraction, a fructose fraction and an organic acid fraction are obtained.

The purification of the product mixture obtained in step e), optionally f) or optionally g) according to step h) is particularly preferably carried out continuously by means of chromatography. Continuous chromatography is preferably also understood to mean simulated chromatography by counterflow, such as, for example, Simulated Moving Bed Chromatography (SMB).

Continuous chromatography methods are well known to the person skilled in the art. For example, US 2011/0137084 A1 shows how the SMB method works. Further suitable chromatography methods are disclosed in A. Rajendran et al.; J. Chromatogr. A 1216 (2009), pages 709 to 738.

Simulated Moving Bed (SMB) systems or further developments of the SMB system, such as Sequential SMB (SSMB), Intermittent/Improved SMB (ISMB) or New MCI (NMCI), advantageously allow the separation and recovery of the four fractions described in continuous operation.

In a preferred embodiment of the present invention, the chromatography, in particular chromatography on ion exchange resins in step h), is a Simulated Moving Bed method (SMB), a Sequential Simulated Moving Bed method (SSMB) or an Improved Simulated Moving Bed method or Intermittent Simulated Moving Bed method (ISMB). Preferably, chromatography, in particular chromatography on ion exchange resins, is in step h) a Simulated Moving Bed method (SMB), a Sequential Simulated Moving Bed method (SSMB), an Improved Simulated Moving Bed method (ISMB) or a New MCI method (NMCI). It is advantageously possible to carry out the purification of the product mixture obtained in step e), f) or g) for the separation of an HMF fraction, a glucose fraction, a fructose fraction and an organic acid fraction in a continuous procedure through the use of a Simulated Moving Bed method (SMB), a Sequential Simulated Moving Bed method (SSMB), an Improved Simulated Moving Bed method (ISMB) or a New MCI method (NMCI) in step h).

In a preferred embodiment of the present invention, the chromatography, in particular chromatography on ion exchange resins, in particular on cation exchange resins in step h), is a one-step process. The chromatography, in particular chromatography on ion exchange resins, in particular on cation exchange resins in step h), is preferably a multi-stage process, preferably a two-stage process.

The chromatography, in particular chromatography on ion exchange resins, in particular on cation exchange resins, in step h) preferably comprises several stages, preferably at least two stages, preferably at least three stages, preferably two stages, preferably three stages.

In a preferred embodiment of the present invention in step h), in a first stage of the chromatography the separation of at least one fraction, preferably exactly one fraction, in particular an HMF fraction or a glucose fraction, preferably at least two fractions, preferably exactly two fractions, preferably exactly three fractions, occurs.

In a further preferred embodiment of the present invention in step h), in a second stage of the chromatography the separation of at least one fraction, preferably exactly one fraction, preferably at least two fractions, preferably exactly two fractions, preferably exactly three fractions, in particular a glucose fraction, a fructose fraction and an organic acid fraction or an HMF fraction, a fructose fraction and an organic acid fraction occurs.

In a preferred embodiment of the present invention, the first stage of the chromatography in step h) is a chromatography method selected from the group consisting of Simulated Moving Bed method (SMB), Sequential Simulated Moving Bed method (SSMB), Improved Simulated Moving Bed method (ISMB) and New MCI method (NMCI).

The first stage of the chromatography in step h) is preferably an improved Simulated Moving Bed method (ISMB). Preferably, in step h) in a first stage the separation of at least one fraction, preferably exactly one fraction, in particular an HMF fraction or an organic acid fraction occurs by means of a chromatography process selected from the group consisting of the Simulated Moving Bed method (SMB), Sequential Simulated Moving Bed method (SSMB), Improved Simulated Moving Bed method (ISMB) and New MCI method (NMCI), preferably using an Improved Simulated Moving Bed method (ISMB).

In a preferred embodiment of the present invention, the second stage of the chromatography in step h) is a chromatography method selected from the group consisting of the Simulated Moving Bed method (SMB), Sequential Simulated Moving Bed method (SSMB), improved Simulated Moving Bed method (ISMB) and New MCI method (NMCI).

The first stage of the chromatography in step h) is preferably a New MCI method (NMCI). Preferably, in step h) in a second stage the separation of at least one fraction, preferably exactly one fraction, preferably at least two fractions, preferably exactly two fractions, preferably at least three fractions, preferably exactly three fractions, in particular a glucose fraction, a fructose fraction and an organic acid fraction or an HMF fraction, a fructose fraction and an organic acid fraction occurs using a chromatographic method selected from the group consisting of the Simulated Moving Bed method (SMB), Sequential Simulated Moving Bed method (SSMB), Improved Simulated Moving Bed method (ISMB) and New MCI method (NMCI), preferably using a New MCI method (NMCI).

In particular, at least two-stage chromatographic separation is preferred, in which the separation of the HMF fraction occurs in the first stage. Alternatively, in the first stage, the separation of the glucose fraction may occur. Preferably, the first stage of the at least two-stage chromatographic separation is a Moving Bed method (ISMB). Preferably, the second stage of the at least two-stage chromatographic separation is preferably a New MCI method (NMCI).

A two-stage chromatographic separation in which the separation of the HMF fraction occurs in the first stage is particularly preferred. Alternatively, in the first stage, the separation of the glucose fraction may occur. Preferably, the first stage of the two-stage chromatographic separation is a Moving Bed method (ISMB). Preferably, the second stage of the two-stage chromatographic separation is a New MCI method (NMCI). Preferably, the organic acid fraction, the fructose fraction and the glucose fraction are separated from one another in the second stage of the two-stage chromatographic separation. Alternatively, in the second stage of the two-stage chromatographic separation, the organic acid fraction, the fructose fraction and the HMF fraction are separated from one another.

In a preferred embodiment of the present invention, chromatography, in particular chromatography on ion exchange resins, in step h) is a chromatography on cation exchange resins.

In a preferred embodiment of the present invention, chromatography, in particular chromatography on ion exchange resins, is carried out in step h) using a cation exchange resin in $H^+$ form.

In a preferred embodiment, chromatography, in particular chromatography on ion exchange resins, is carried out in step h) at a temperature of 40° C. to 80° C., preferably 40° C. to 70° C., preferably 40° C. to 60° C., preferably 50° C. to 80° C., preferably 50° C. to 70° C., preferably 50° C. to 60° C., preferably 60° C. to 80° C., preferably 60° C. to 70° C.

The fructose fraction optionally obtained in step i) is preferably continuously recycled to method step a). The fructose fraction optionally obtained in step i) is advantageously largely, preferably completely, freed from levulinic acid being formed. In a further preferred embodiment, the fructose fraction obtained in step i) is advantageously largely, preferably completely, freed from levulinic and formic acid being formed.

In a particularly preferred embodiment, the fructose fraction optionally obtained in step i), optionally after concentration, is continuously and preferably completely recycled to step a). In a further preferred embodiment, the fructose fraction obtained in step i) is continuously, optionally after concentration, at least partially recycled in step a), in particular to at least 70%, preferably to at least 80%, preferably to at least 90%, preferably to at least 95%, preferably to at least 98%, preferably to at least 99%, (in each case wt.-% of the recycled fructose fraction in relation to the fructose fraction obtained in step i)).

According to the invention, a "recycled fructose fraction" is understood to mean an aqueous fraction of unconverted fructose that may be obtained after the purification carried out according to the method according to the invention, i.e., step h), which is largely, preferably completely, free of byproducts formed during fructose conversion, in particular levulin and formic acid and humic substances. The resulting aqueous fraction of unreacted fructose is so pure that in a preferred embodiment it is recycled directly to method step a), optionally after concentration, i.e., without further purification, and after mixing with the fructose-containing component and the catalyst system, that is to say step b), is available for a further conversion to HMF in step c). Step a) of the method according to the invention therefore particularly preferably provides for a fructose-containing component, a salt and acid mixture and a recycled fructose fraction, which are mixed in step b) to obtain a reaction solution. Since in this preferred embodiment there is initially no recycled fructose fraction available when the method according to the invention is initiated, a correspondingly larger amount of the fructose-containing component is preferably used instead in this case.

In step i) of the method according to the invention, i.e., after the purification has been carried out, a glucose fraction, a fructose fraction and an organic acid fraction are optionally obtained, in particular in isolated form, in addition to the fraction. Advantageously, the individual fractions obtained using the purification methods used have such high purities that they can be used directly in various subsequent processes, optionally after concentration, i.e. without further purification.

According to the invention, the optionally obtained fructose fraction is preferably largely free, in particular completely free, of levulinic acid being formed. According to the invention, the fructose fraction obtained is preferably largely free, in particular completely free from organic acids being formed, in particular levulinic and formic acid.

Levulinic acid disadvantageously favors the formation of humic substances during HMF synthesis. Thus, an increased content of levulinic acid in the reaction solution caused by the fructose fraction recycled according to a preferred embodiment would lead to an increased formation of humic substances from HMF and carbohydrates and thus significantly reduce the economic efficiency of the method. The fructose fraction optionally obtained in step i) in the method according to the invention has, however, advantageously such a high purity, is in particular free from levulinic acid being formed, particularly preferably free from levulinic and formic acid, that in a preferred embodiment it can be recycled directly to the process, in particular to step a) for further conversion, optionally after concentration, in particular without purification steps. In particular, the limited conversion of fructose provided by the method according to the invention and the associated reduced formation of byproducts and degradation products, in particular levulinic and formic acid and humic substances, and in a preferred embodiment, the recycling of a fraction separated from the product mixture of unconverted fructose, leads to a high HMF selectivity and a high HMF yield.

In a particularly preferred embodiment, the method according to the invention consists of method steps a), b), c) and d), in particular no further method steps are carried out, between these method steps.

In a particularly preferred embodiment of the present invention, the method according to the invention comprises method steps a), b), c) and d), wherein no further method steps are carried out between method steps a), b), c) and d), but optionally after method step d) is carried out, further method steps are carried out.

According to the invention, the present method comprises steps a) to d), preferably a) to e), preferably a) to f), preferably a) to g), preferably a) to h), in particular a) to i). According to the invention, the present method particularly preferably comprises steps a), b), c), d), e), f), g), h) and i). However, it can also be provided that the present method includes steps a), b), c), d), e), h) and i) or a), b), c), d), e), f), h) and i) or a), b), c), d), e), g) h) and i). In a particularly preferred embodiment, the present method consists of method steps a) to d), preferably a) to e), preferably a) to f), preferably a) to g), preferably a) to h), in particular a) to i). In a particularly preferred embodiment, the present method consists of method steps a), b), c), d), e), h) and i) or a), b), c), d), e), f), h) and i) or a), b), c), d), e), g) h) and i). In a preferred embodiment, the method is carried out in the order of method steps a), b), c), d), e), f), g), h) and i). However, it can also be provided that the present method is carried out in the order of method steps a), b), c), d), e), h) and i) or a), b), c), d), e), f), h) and i) or a), b), c), d), e), h) and i).

According to the invention, in the method for the production of 5-hydroxymethylfurfural according to steps a) to i), the conversion of fructose present in the reaction mixture to HMF in a continuous reactor system and the subsequent purification of the product mixture obtained for the separation of at least four fractions occur continuously, i.e. with constant supply of starting materials and removal of products.

A continuous process according to the invention is preferably understood to mean a process in which not only the reactor system, but also the purification of the product mixture is continuous.

The present invention enables the provision of methods for the production of HMF and/or formic acid and/or levulinic acid, in particular for the simultaneous production from a starting material, namely a fructose-containing component and optionally a recycled fructose fraction.

In a preferred embodiment, the method according to the invention for the production of HMF is therefore also a method for the production of HMF and formic acid and levulinic acid, which comprises steps a) to i) and is used for the targeted production of three products of interest.

In a preferred embodiment, the method according to the invention for the production of HMF is therefore also a method for the production of HMF and formic acid, which comprises steps a) to i) and which serves to produce two valuable substances of interest.

In a preferred embodiment, the method for the production of HMF according to the invention is therefore also a method for the production of HMF and levulinic acid, which comprises steps a) to i) and which is used to produce two valuable substances of interest.

According to the invention, the glucose fraction obtained in step i) comprises at least 20 wt.-% of the glucose contained in the product mixture (in each case DM based on the product mixture).

In a further preferred embodiment of the present invention, the glucose fraction optionally obtained in step i) has a sufficiently high purity, is in particular free from fermentation inhibitors, so that it can be used directly, optionally after concentration, both as a feed (feed material) in fermentative processes, in particular for the production of ethanol, in particular glucose fermentation to ethanol, and as a starting material in chemical processes, in particular the oxidation of glucose to gluconic acid.

In a further preferred embodiment, the glucose fraction optionally obtained in step i) is used for ethanol production, in particular glucose fermentation to form ethanol, in particular for bio-ethanol production, and/or for gluconic acid production.

The present invention therefore also provides a method for the production of a feed for fermentative processes, in particular for the production of ethanol, in particular glucose fermentation to ethanol, or for the production of a starting material, that is to say an educt, in chemical processes, in particular for the production of gluconic acid, in the context of which a method of the present invention is carried out with method steps a) to i) while obtaining a glucose fraction which can be used as feed or educt.

In a particularly preferred embodiment, a method for ethanol production, in particular the fermentation of glucose to ethanol, is provided, in the context of which the method according to the invention, in particular method steps a) to i), in particular for obtaining a glucose fraction, are carried out, wherein the glucose fraction obtained is used for the production of ethanol, in particular the fermentation of glucose to ethanol, in particular for the production of bio-ethanol.

In a further preferred embodiment, the glucose fraction optionally obtained in step i) is used to obtain gluconic acid, optionally after concentration.

In a particularly preferred embodiment, a method for the production of gluconic acid is provided, which comprises the method according to the invention, in particular method steps a) to i), in particular for obtaining a glucose fraction that is used to obtain glucose and to subsequently oxidize glucose to gluconic acid.

In a preferred embodiment of the present invention, the organic acid fraction optionally obtained in step i) is used to isolate levulinic and formic acid. In a further preferred embodiment, the organic acid fraction obtained in step i) is used to isolate levulinic acid. In a further preferred embodiment, the organic acid fraction obtained in step i) is used to isolate formic acid.

The present invention therefore also relates to a method for the production of levulinic acid, formic acid or levulinic acid and formic acid, wherein a method comprising steps a) to i) of the present invention is carried out and levulinic acid, formic acid or levulinic acid and formic acid are obtained in a step i).

In a further preferred embodiment of the present invention, the HMF fraction obtained in step i) is oxidized directly in an additional step to 2,5-furandicarboxylic acid (FDCA), optionally after concentration, i.e., without the need for work-intensive further purification.

The present invention therefore also relates to a method for the production of FDCA, comprising steps a) to i) of the present invention, wherein the HMF fraction obtained in step i) is oxidized to FDCA, preferably directly, optionally after concentration, and without the need for work-intensive further purification.

According to the invention, the glucose fraction optionally obtained contains 0.8 wt.-% to 100 wt.-% glucose, 0 wt-% to 99.2 wt.-% fructose, at most 2 wt.-%, preferably at most 1 wt.-%, preferably at most 0.5 wt.-%, preferably at most 0.1 wt.-%, levulinic and formic acid and at most 10 wt.-%, preferably at most 5 wt.-%, preferably at most 2 wt.-%, more preferably at most 1 wt.-%, preferably at most 0.5 wt.-%, preferably at most 0.1 wt.-%, HMF (in each case DM, based on the total of the components analyzed (glucose, fructose, levulinic acid, formic acid, HMF, difructose anhydrides (DFA)). According to the invention, the glucose fraction preferably contains at most 10 wt.-%, more preferably at most 5 wt.-% HMF.

The fructose fraction optionally obtained in step i) according to the invention contains at least 70 wt.-%, preferably at least 80 wt.-%, of the fructose contained in the product mixture (in each case DM based on the product mixture).

According to the invention, the optionally obtained fructose fraction contains 0 wt.-% to 60 wt.-% glucose, 40 wt.-% to 100 wt.-% fructose, at most 2 wt.-%, preferably at most 1 wt.-%, preferably at most 0.5 wt.-%, preferably at most 0.1 wt.-%, levulinic acid, at most 2 wt.-%, preferably at most 1.5 wt.-%, preferably at most 1 wt.-%, preferably at most 0.5 wt.-%, preferably at most 0.25 wt.-%, preferably at most 0.1 wt.-%, formic acid and at most 2 wt.-%, preferably at most 1.5 wt.-%, preferably at most 1 wt.-%, preferably at most 0.8 wt.-%, preferably at most 0.6 wt.-%, preferably at most 0.4 wt.-%, preferably at most 0.2 wt.-%, preferably at most 0.1 wt.-% HMF (in each case DM, based on the total of the components analyzed (glucose, fructose, levulinic acid, formic acid, HMF, difructose anhydrides (DFA)). According to the invention, the fructose fraction preferably contains at most 2 wt.-% HMF. According to the invention, the fructose fraction preferably contains at most 2 wt.-% levulinic acid. In a particularly preferred embodiment, the ratio of fructose to glucose in the fructose fraction is not less than in the fructose-containing component provided in step a).

According to the invention, the organic acid fraction optionally obtained in step i) contains at least 60 wt.-%, preferably at least 65 wt.-%, preferably at least 70 wt.-%, preferably at least 80 wt.-%, preferably at least 90 wt.-%, preferably at least 95 wt.-%, preferably at least 98 wt.-%, preferably at least 99 wt.-%, preferably at least 99.5 wt.-%, preferably at least 99.8 wt.-%, preferably 100 wt.-% of the levulinic and formic acid contained in the product mixture (in each case DM, based on the product mixture).

According to the invention, the organic acid fraction optionally obtained contains 50 wt.-% to 100 wt.-%, preferably 60 wt.-% to 100 wt.-%, preferably, more preferably 65 wt.-% to 100 wt.-%, preferably 70 wt.-% to 100 wt.-%, preferably 80 wt.-% to 100 wt.-%, preferably 90 wt.-% to 100 wt.-%, preferably 95 wt.-% to 100 wt.-%, preferably 98 wt.-% to 100 wt.-%, preferably 99 wt.-% to 100 wt.-%, preferably 99.5 wt.-% to 100 wt.-%, preferably 99.7 wt.-% to 100 wt.-% of levulinic and formic acid (in each case DM, based on the total of the components analyzed (glucose, fructose, levulinic acid, formic acid, HMF, difructose anhydrides (DFA)). According to the invention, the organic acid fraction preferably contains at least 50 wt.-% of levulinic acid, more preferably at least 60 wt.-% of levulinic acid, more preferably at least 70 wt.-% of levulinic acid.

According to the invention, the HMF fraction obtained in step i) contains at least 70 wt.-%, preferably at least 80 wt.-%, more preferably at least 90 wt.-%, preferably at least 98 wt.-%, preferably at least 99 wt.-%, preferably at least 99.5 wt.-%, preferably at least 99.8 wt.-%, preferably 100 wt.-% of the HMF contained in the product mixture (in each case DM, based on the product mixture).

According to the invention, the HMF fraction contains 80 wt.-% to 100 wt.-%, preferably 85 wt.-% to 100 wt.-%, preferably 90 wt.-% to 100 wt.-%, preferably 95 wt.-% to 100 wt.-%, preferably 98 wt.-% to 100 wt.-%, preferably 99 wt-% to 100 wt.-%, preferably 99.5 wt.-% to 100 wt.-%, preferably 99.7 wt.-% to 100 wt.-% HMF and at most 16 wt.-%, preferably at most 14 wt.-%, preferably at most 12 wt.-%, preferably at most 10 wt.-%, preferably at most 8 wt.-%, preferably at most 6 wt.-%, preferably at most 4 wt.-%, preferably at most 2 wt.-%, preferably at most 1 wt.-%, levulinic and formic acid, at most 2 wt.-%, preferably at most 1 wt.-%, preferably at most 0.8 wt.-%, preferably at most 0.6 wt.-%, preferably at most 0.4 wt.-%, preferably at most 0.2 wt.-%, preferably at most 0.1 wt.-%, glucose and at most 2 wt.-%, preferably at most 1 wt.-%, preferably at most 0.8 wt.-%, preferably at most 0.6 wt.-%, preferably at most 0.4 wt.-%, preferably at most 0.2 wt.-%, preferably at most 0.1 wt-% fructose (in each case DM, based on the total of the components analyzed (glucose, fructose, levulinic acid, formic acid, HMF, difructose anhydrides (DFA)).

In a preferred embodiment, no organic solvents, in particular no ionic liquids, are used in the method according to the invention, in particular during steps a) to g), optionally a) to i).

In a preferred embodiment, the method according to the invention, in particular during steps a) to i), is not carried out under oxygen-reduced conditions.

In connection with the present invention, the term "and/or" is understood to mean that all members of a group which are connected by the term "and/or" are disclosed both as alternatives to one another and also cumulatively to one another in any combination. For the expression "A, B and/or C," this means that the following disclosure content is to be understood: A or B or C or (A and B) or (A and C) or (B and C) or (A and B and C).

In connection with the present invention, the term "comprehensive" is understood to mean that in addition to the elements explicitly covered by the term, further elements that are not explicitly mentioned can be added. In connection with the present invention, these terms are also understood to mean that only the explicitly mentioned elements are included and no further elements are present. In this particular embodiment, the meaning of the term "comprising" is synonymous with the term "consisting of." In addition, the term "comprehensive" also includes entities that, in addition to the explicitly named elements, also contain other elements that are not named, but which are functionally and qualitatively subordinate. In this embodiment, the term "comprising" is synonymous with the term "consisting substantially of."

Further preferred embodiments are particularly found in the dependent claims.

The invention is explained in more detail with reference to the following exemplary embodiments and the associated figures.

The figures show:

EXAMPLES

In the method according to the invention, a fructose-containing component which has a variable ratio of fructose to glucose and an aqueous solution of a salt and acid mixture are used as starting materials. The fructose-containing component is mixed with the aqueous solution of a salt and acid mixture so that a reaction solution with a dry matter content of ≥20% DM is obtained. The reaction solution obtained in this way was pumped into the heated tubular reactor (outer diameter 8 mm, inner diameter 6 mm, length 630 mm) with the aid of an HPLC pump. The tubular reactor is designed as a double tube heat exchanger in counterflow, the temperature is controlled by means of a thermal oil in the outer jacket of the heat exchanger, the temperature of the thermal oil is controlled by a thermostat. After this so-called heating zone of the tubular reactor, the transition to the cooling zone occurs directly. This is also designed as a double-tube heat exchanger in counterflow (dimensions of the product-carrying inner tube: outer diameter 8 mm, inner diameter 6 mm, length 125 mm). The reaction solution is cooled to room temperature within the cooling zone and the conversion is stopped. The product mixture is then filtered through a metal sinter filter (pore size 7 μm) and any insoluble humic substances that may have formed are removed. The pressure in the reactor system is set with the aid of a pressure holding valve so that boiling of the reaction solution and thus the occurrence of vapor bubbles is avoided (approx. 1 MPa at 180° C.).

The following examples show the implementation of the method according to the invention with different salts and acids, different acid or salt concentrations, and at different temperatures. Furthermore, comparative experiments were carried out without the addition of salt.

In all experiments, samples were taken during the test and analyzed by means of HPLC (BIORAD Aminex 87-H, 5 mmol/L sulfuric acid, 50° C.). Fructose conversion, HMF selectivity and the balance (balance=(total of unconverted sugar, HMF and formic acid (in mol)*100/sugar used (in mol)) were subsequently calculated from the analytical results. Levulinic acid is not taken into account in the balance, since one molecule of formic acid and one molecule of levulinic acid are produced from one molecule of HMF.

Example 1: HMF Synthesis with 0.08 wt.-% Hydrochloric Acid (Comparative Experiment Without Added Salt)

Figure 1:
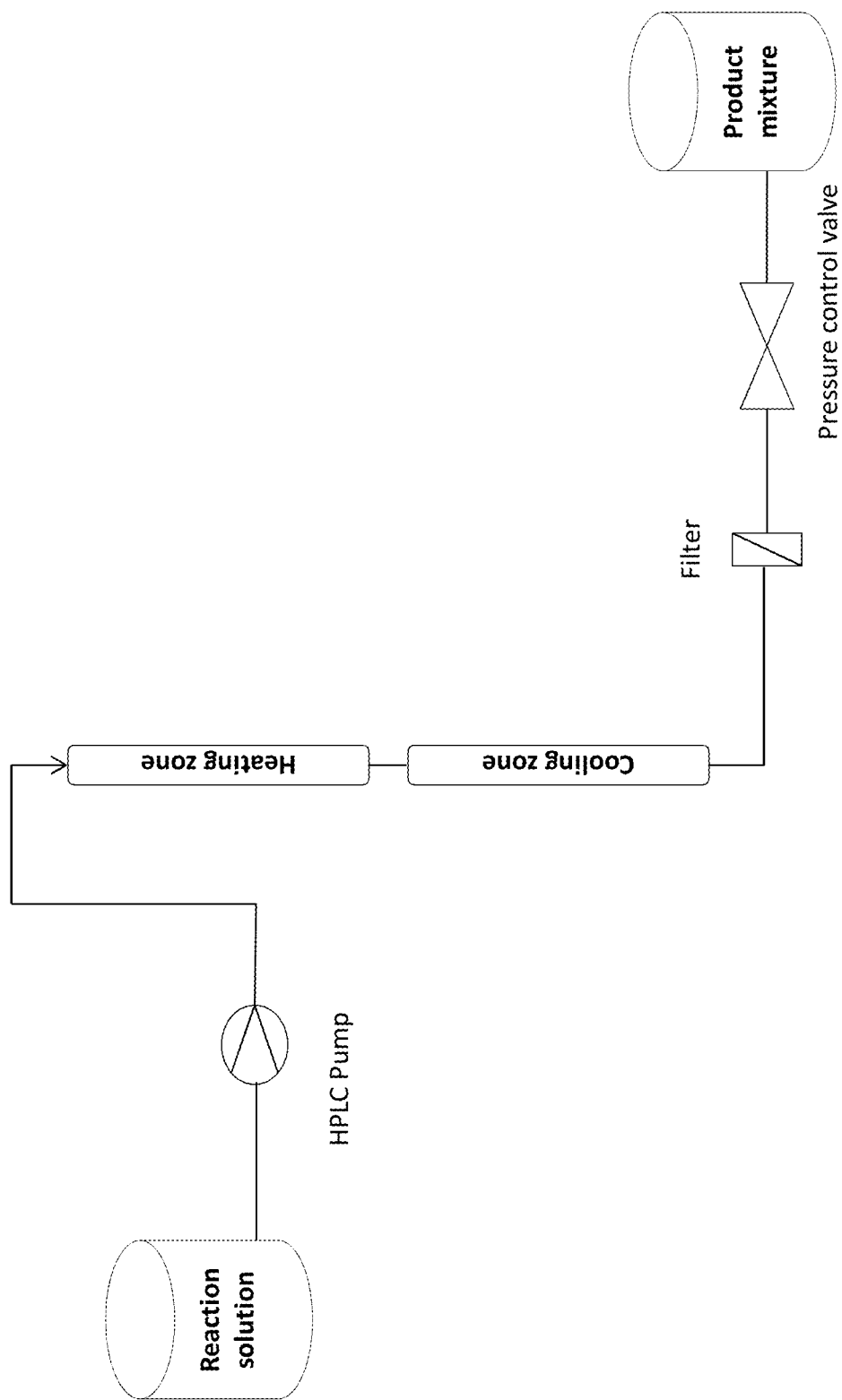
FIG. 1 is a schematic representation of the reactor system used according to the invention.
Figure 2:
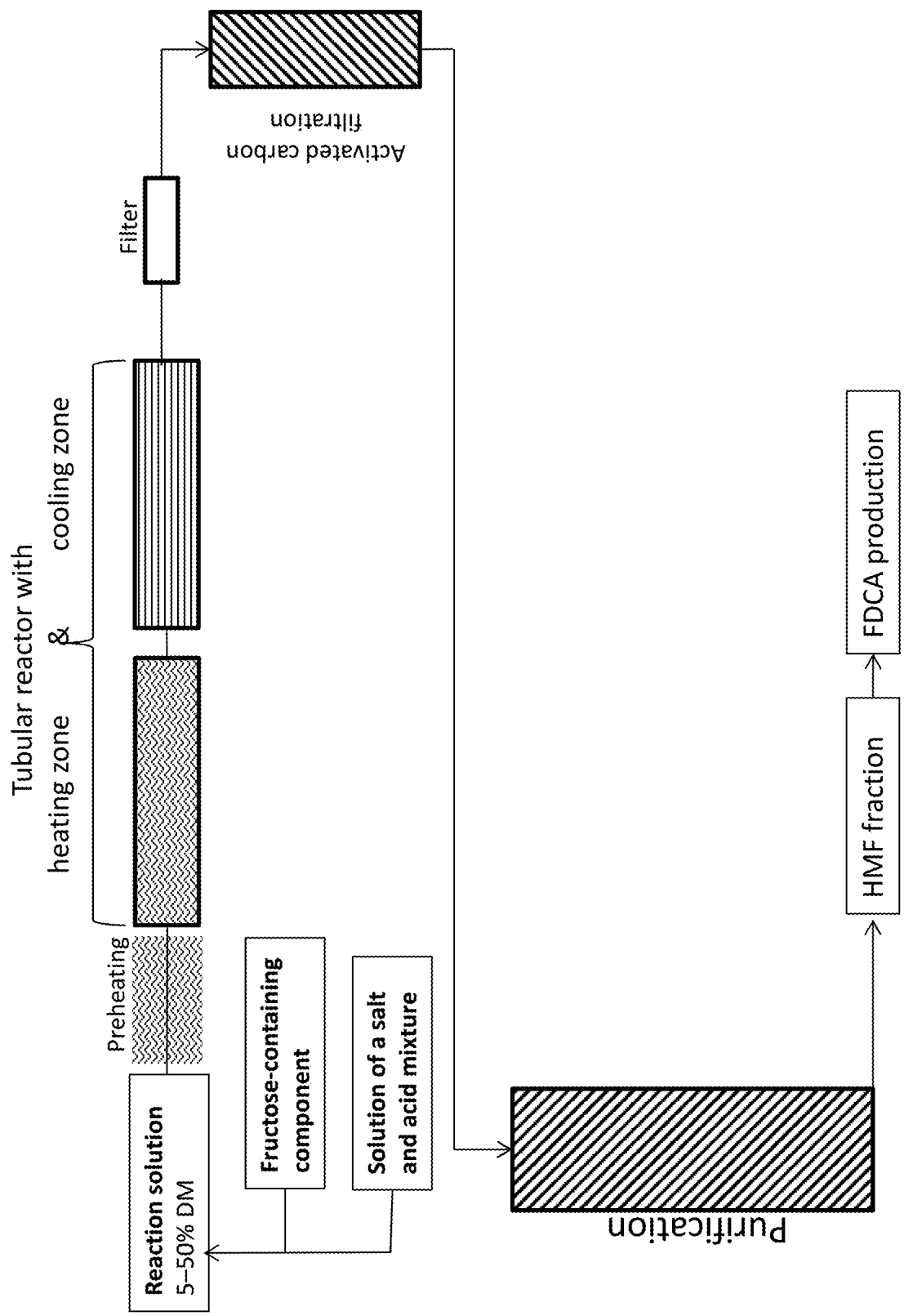
FIG. 2 is a schematic representation of the method according to the invention, wherein the components provided in step a) are initially mixed in step b) and the reaction solution obtained is subsequently heated and an HMF fraction is obtained after the purification step h) (step i)).
Figure 3:
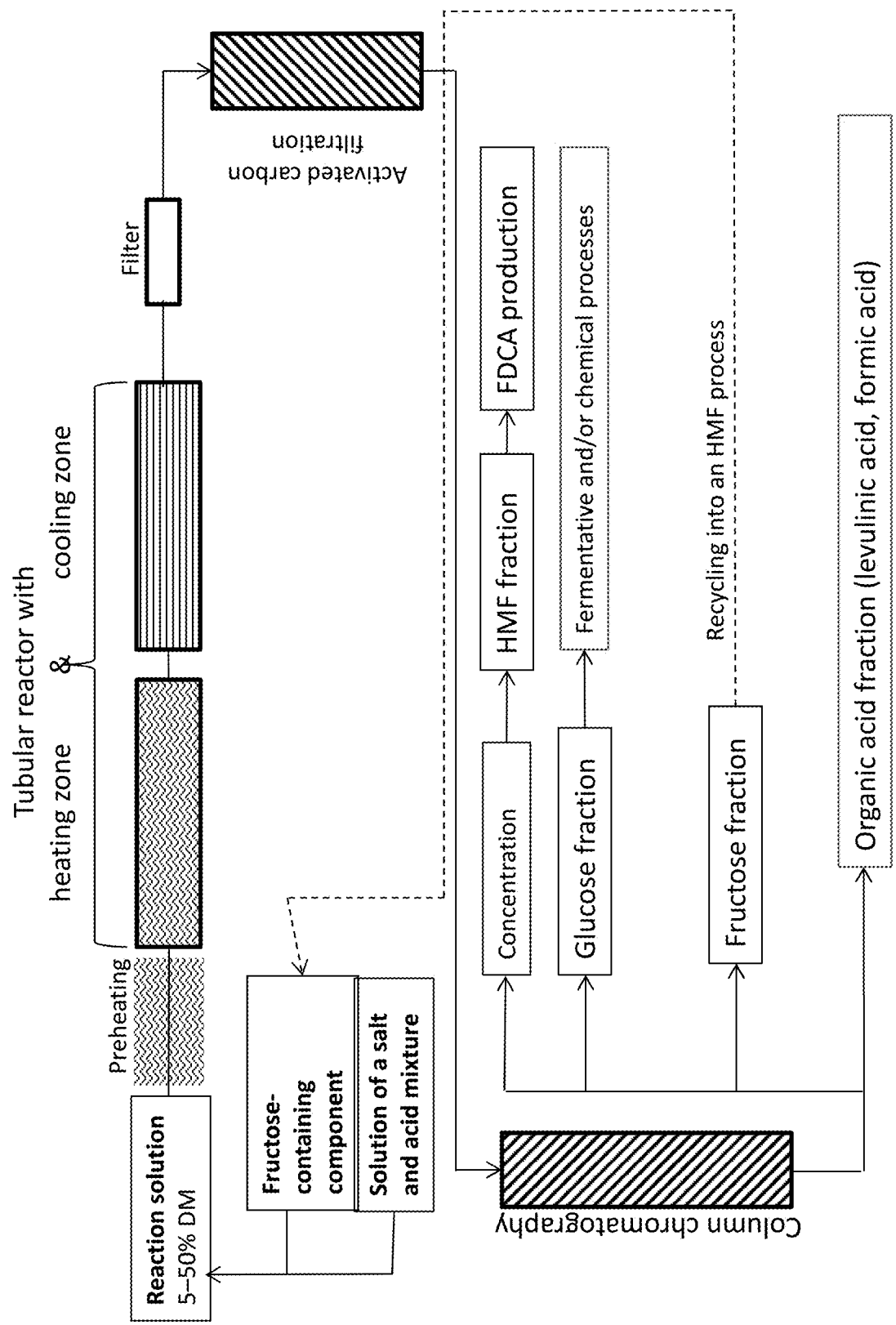
FIG. 3 is a schematic representation of the method according to the invention analogous to FIG. 2, wherein in step h) a column chromatographic separation is carried out and an HMF fraction, a glucose fraction, a fructose fraction and an organic acid fraction are obtained (step i)).
Figure 4:
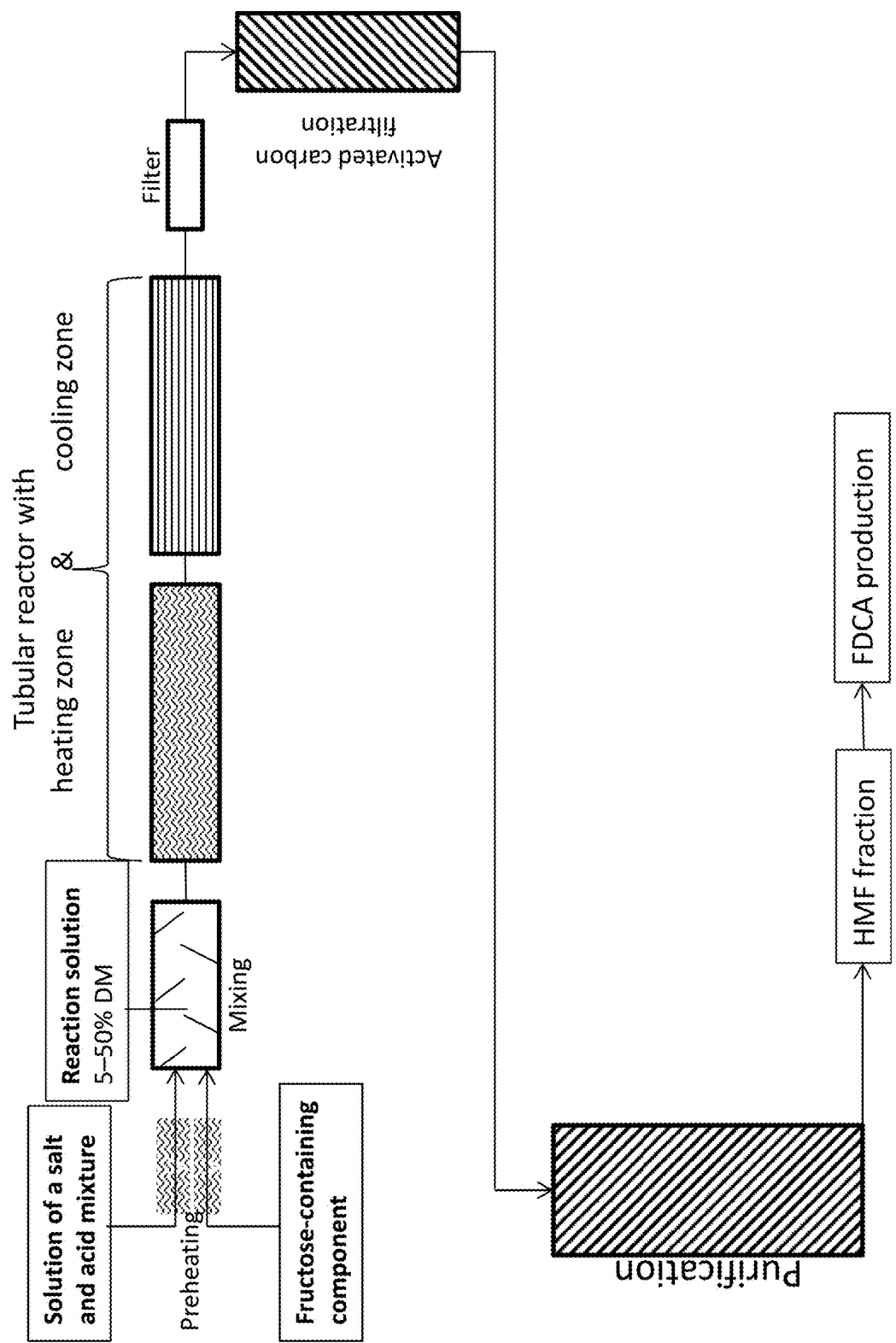
FIG. 4 is a schematic representation of the method according to the invention, wherein the components provided in step a) are heated separately from one another and only subsequently mixed in step b) to obtain a reaction solution, and wherein an HMF fraction is obtained after purification step h) (step i)).
Figure 5:
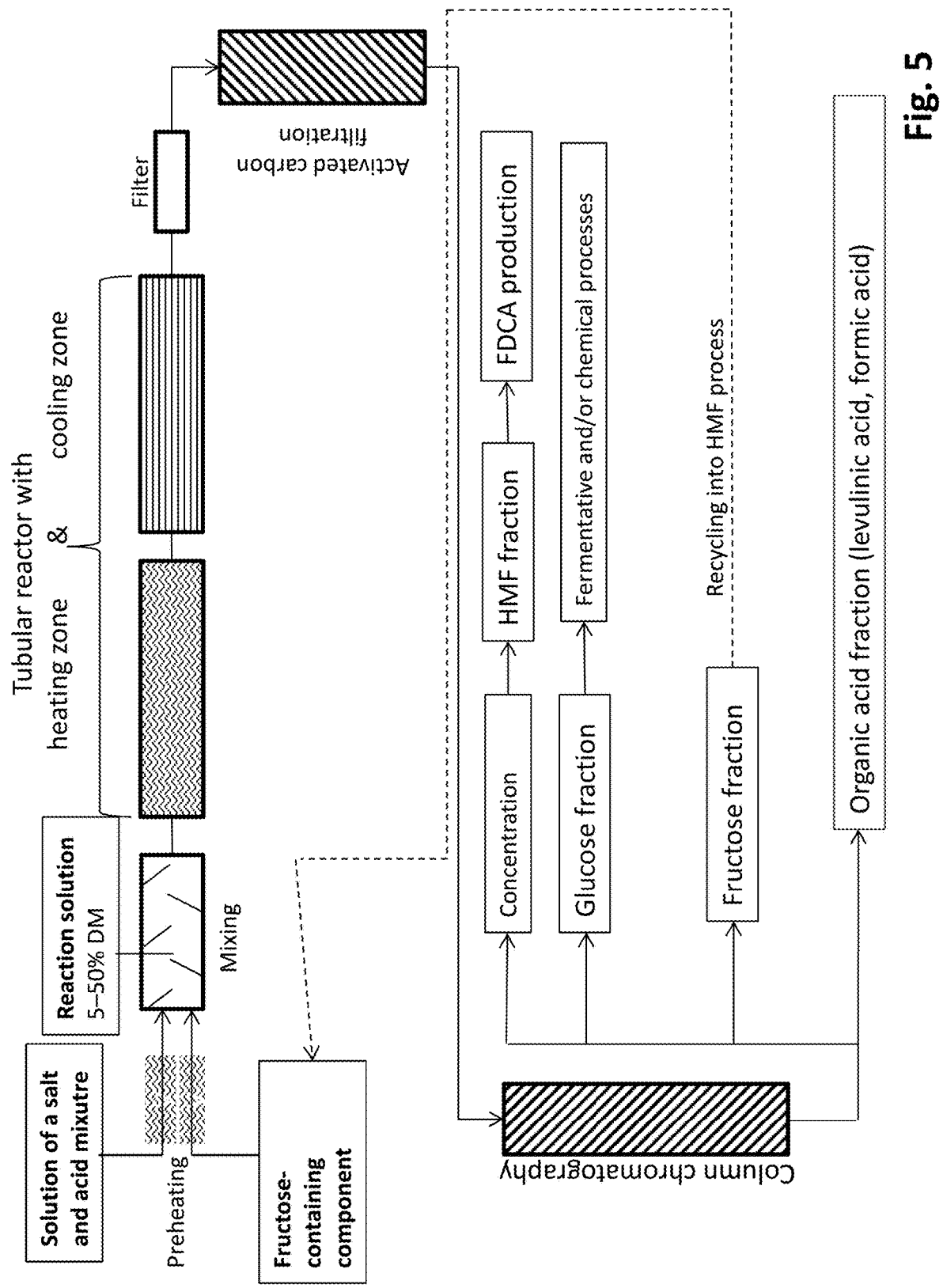
FIG. 5 is a schematic representation of the method according to the invention analogous to FIG. 4, wherein a column chromatographic separation is carried out in step h) and an HMF fraction, a glucose fraction a fructose fraction and an organic acid fraction are obtained (step i)).
Figure 6:
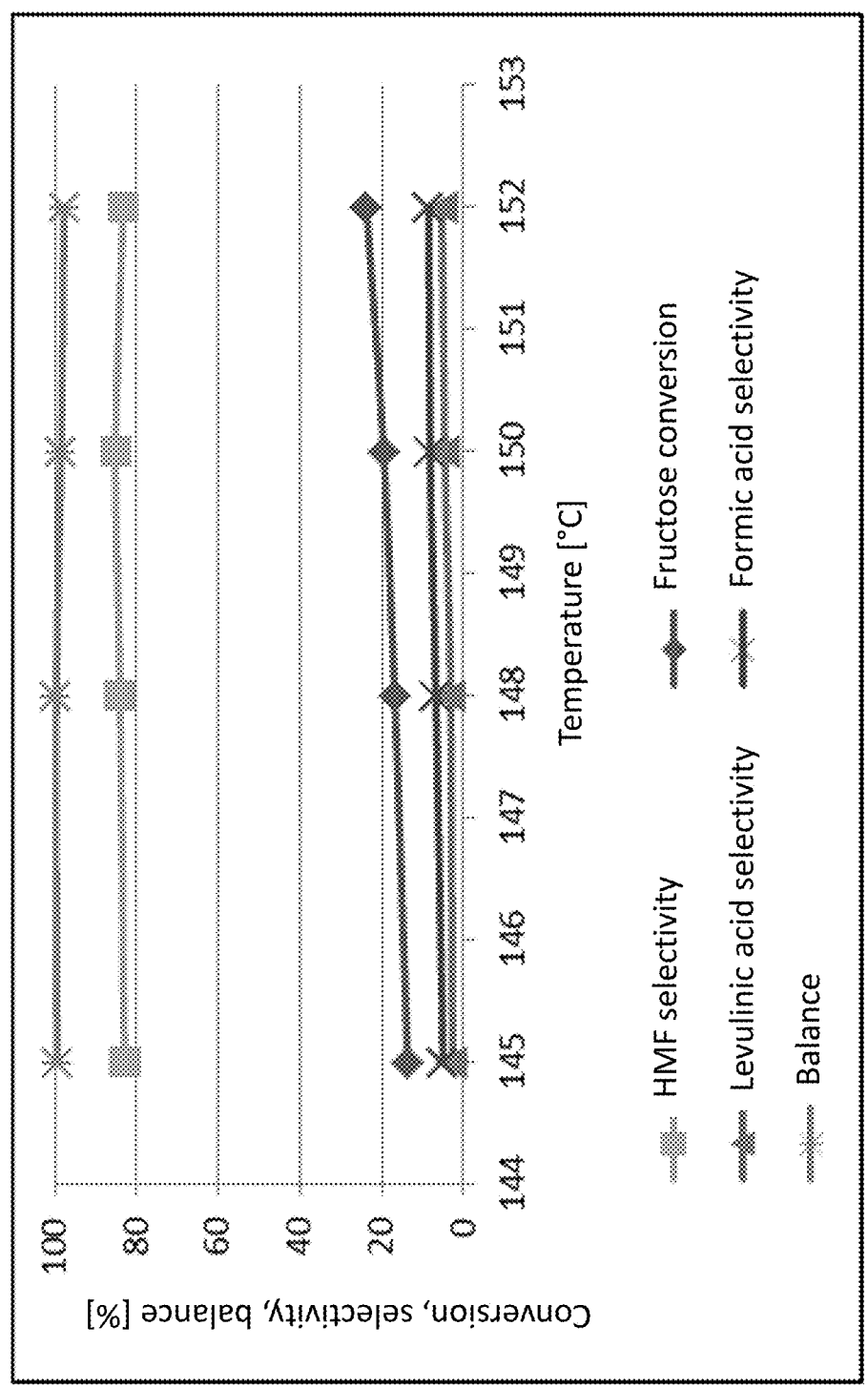
FIG. 6 shows the results of the HMF synthesis with 20% DM KH (85% fructose purity) and 0.08 wt.-% HCl without the addition of salt at temperatures of 145-152° C. Fructose conversion, HMF, levulinic acid and formic acid selectivity and the balance are represented.

A fructose syrup with 85% fructose purity and a DM content of 75% was used as starting material. The fructose syrup was diluted with deionized water and mixed with hydrochloric acid so that the resulting solution had a dry matter content of 20% DM and a hydrochloric acid content of 0.08 wt.-% based on the total solution (corresponding to 0.025 mol/L). The pH of the reaction solution was 1.52. This reaction solution was then reacted with a residence time of 5.6 min. in the heating zone at a temperature of 145° C.-152° C. (temperature of the thermal oil). After each temperature increase, the system was given 2 hours to reach steady state. The results on fructose conversion, HMF, levulinic acid and formic acid selectivity and balance are shown in FIG. 6 and Table 1.

TABLE 1

Fructose conversion, HMF, levulinic acid and formic acid selectivity and balance as a function of the reaction temperature when using 0.08 wt-% of HCl.

| Temperature [° C.] | Fructose conversion [%] | HMF selectivity [%] | Levulinic acid selectivity [%] | Formic acid selectivity [%] | Balance [%] |
|---|---|---|---|---|---|
| 145 | 13.7 | 83.0 | 2.7 | 5.0 | 99.6 |
| 148 | 16.9 | 84.1 | 3.2 | 6.8 | 99.7 |
| 150 | 19.6 | 85.2 | 4.6 | 8.2 | 98.5 |
| 152 | 23.8 | 83.3 | 5.3 | 8.2 | 97.8 |

Example 2: HMF Synthesis with 0.18 wt.-% Nitric Acid (Comparative Experiment Without Added Salt)

Figure 7:
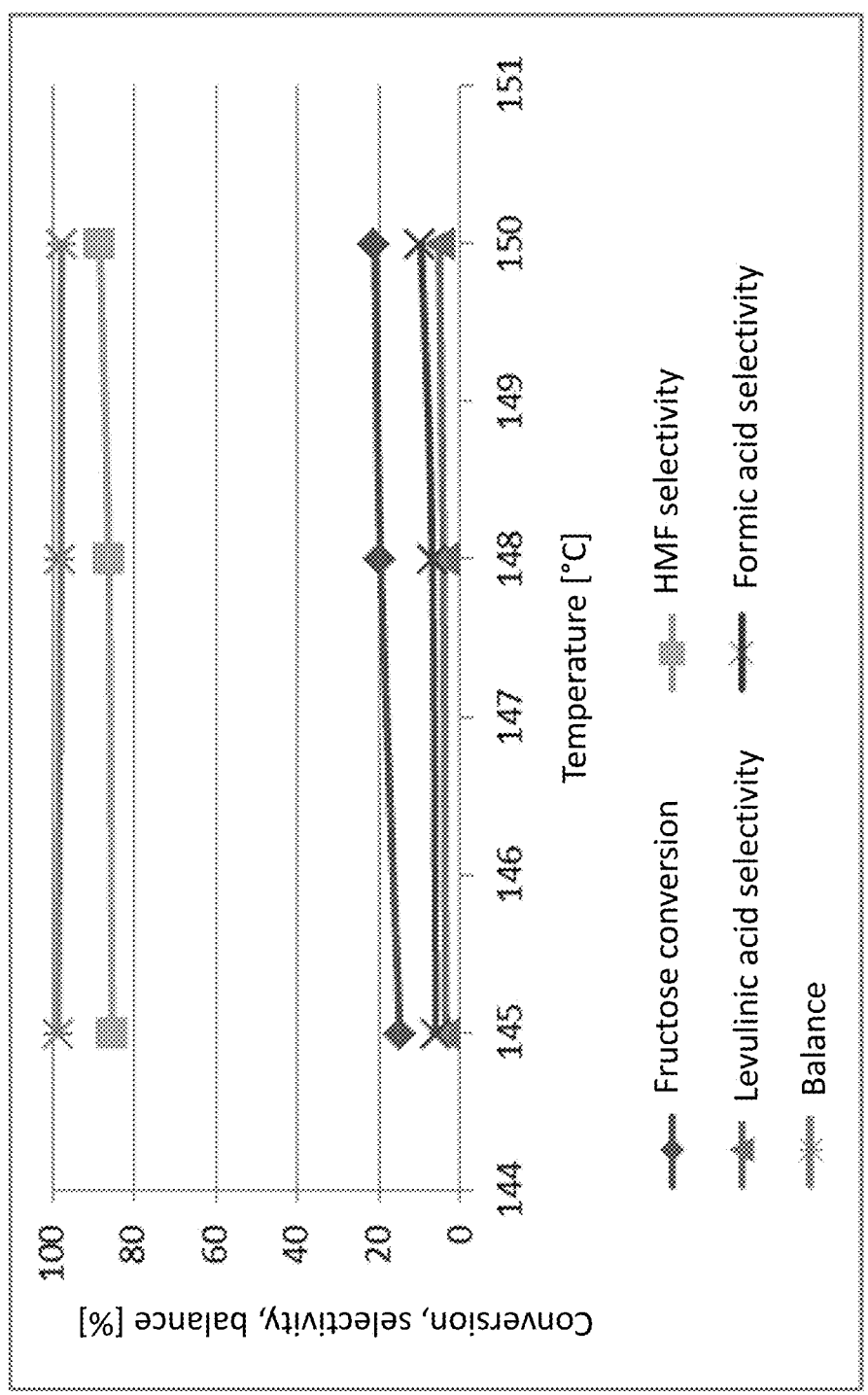
FIG. 7 shows the results of the HMF synthesis with 20% DM KH (85% fructose purity) and 0.18 wt.-% $HNO_3$ without addition of salt at temperatures of 145-152° C. Fructose conversion, HMF, levulinic acid and formic acid selectivity and the balance are represented.

A fructose syrup with 85% fructose purity and a DM content of 75% was used as starting material. The fructose syrup was diluted with deionized water and mixed with nitric acid so that the resulting solution had a dry matter content of 20% DM and a nitric acid content of 0.18 wt.-% based on the total solution (corresponding to 0.03 mol/L). The pH of the reaction solution was 1.44. This reaction solution was then converted with a residence time of 5.6 min in the heating zone at a temperature of 145° C.-150° C. (temperature of the thermal oil). After each temperature increase, the system was given 2 hours to reach steady state. The results on fructose conversion, HMF, levulinic acid and formic acid selectivity and balance are shown in FIG. 7 and Table 2.

TABLE 2

Fructose conversion, HMF, levulinic acid and formic acid selectivity and balance depending on the reaction temperature when using 0.18 wt.-% of $HNO_3$.

| Temperature [° C.] | Fructose conversion [%] | HMF selectivity [%] | Levulinic acid selectivity [%] | Formic acid selectivity [%] | Balance [%] |
|---|---|---|---|---|---|
| 145 | 15.0 | 85.4 | 3.6 | 6.1 | 98.7 |
| 148 | 19.7 | 86.3 | 4.2 | 7.0 | 98.0 |
| 150 | 21.1 | 88.4 | 5.2 | 9.8 | 97.8 |

Example 3: HMF Synthesis with Sodium Chloride/Hydrochloric Acid Mixtures—Influence of the Sodium Chloride/Hydrochloric Acid Ratio A fructose syrup with 85% fructose purity and a DM content of 75% was used as starting material. The fructose syrup was diluted with deionized water and mixed with hydrochloric acid and sodium chloride in the desired ratio so that the resulting solution had a dry matter content of 20% DM and a chloride content of 0.09 wt.-% based on the total solution (corresponding to 0.03 mol/L). The chloride/sodium ratios, the salt/acid ratio and the resulting pH values are indicated in Table 3.

TABLE 3

Chloride contents, chloride/sodium ratio, salt/acid ratio and pH values and reaction temperatures used in the reaction solutions used in Example 3.

| Test | Chloride content [mg/L] | Sodium content [mg/L] | Ratio chloride/sodium [mol/mol] | Ratio salt/acid [mol/mol] | pH [—] | Reaction temperatures [° C.] |
|---|---|---|---|---|---|---|
| 1 | 890 | 0 | / | / | 1.52 | 145-152 |
| 2 | 890 | 330 | 1.75 | 1.34 | 1.95 | 160-168 |
| 3 | 890 | 400 | 1.44 | 2.26 | 2.24 | 165-172 |
| 4 | 890 | 490 | 1.15 | 6.48 | 2.52 | 169-176 |

These reaction solutions were then converted with a residence time of 5.6 min. in the heating zone at the reaction temperatures indicated in Table 3 (temperature of the thermal oil). After each temperature increase, the system was given 2 hours to reach steady state.

Figure 8:
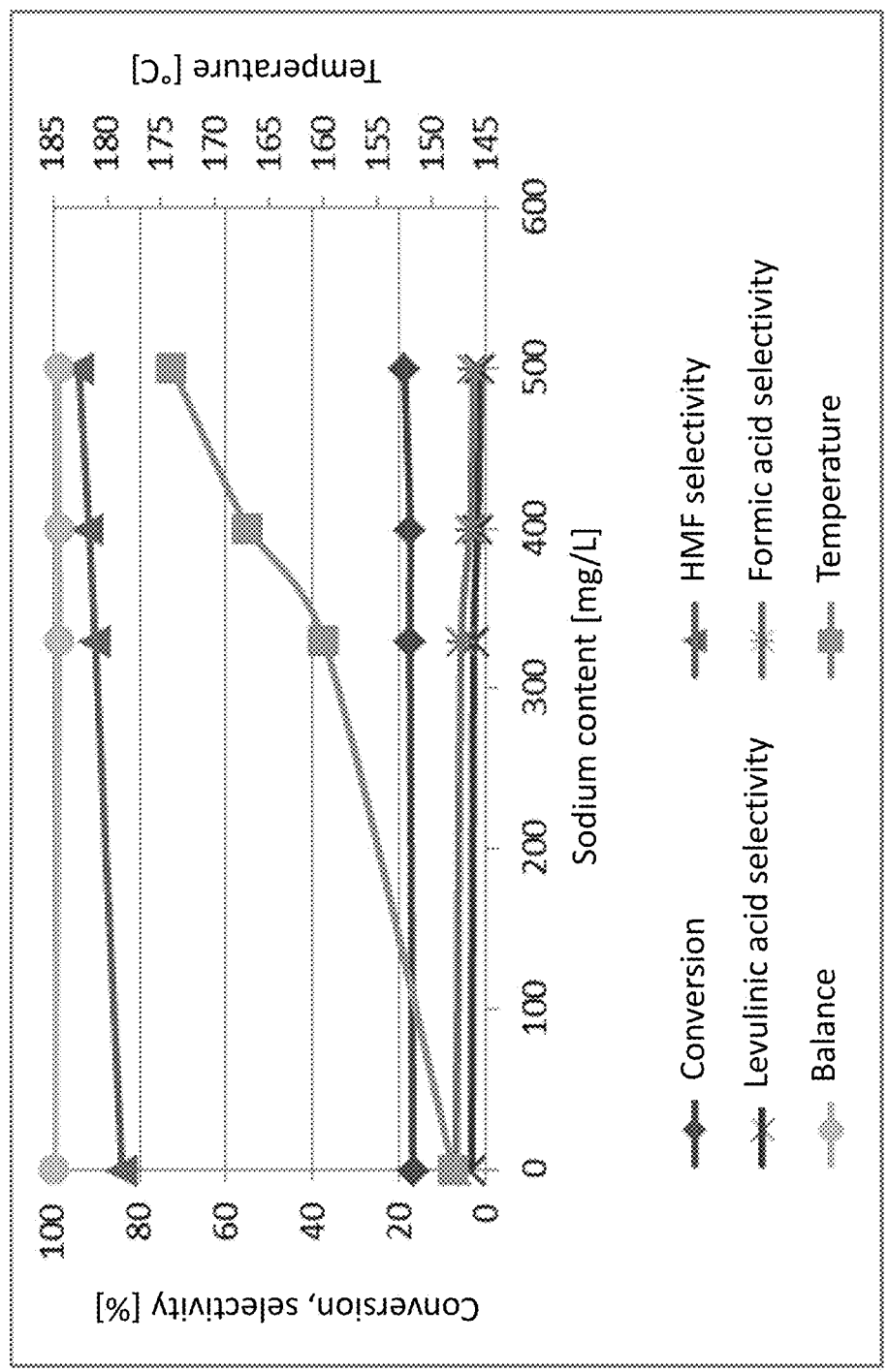
FIG. 8 shows the reaction temperatures which are necessary for a fructose conversion of ~18% as a function of the sodium content with a constant chloride content as well as HMF, levulinic acid and formic acid selectivities and the balance at this point.

In FIG. 8 and Table 4, the necessary reaction temperatures and the resulting HMF, levulinic acid and formic acid selectivities and balances are shown in each case at a fructose conversion of ~18%.

TABLE 4

HMF, levulinic acid and formic acid selectivity and balance at the reaction temperature necessary
for 18% fructose conversion depending on the sodium content (with constant chloride concentration).

| Sodium content [mg/L] | Temperature [° C.] | Fructose conversion [%] | HMF selectivity [%] | Levulinic acid selectivity [%] | Formic acid selectivity [%] | Balance [%] |
|---|---|---|---|---|---|---|
| 0 | 145 | 13.7 | 83.0 | 2.7 | 5.0 | 99.6 |
| (pH 1.52) | 148 | 16.9 | 84.1 | 3.2 | 6.8 | 99.7 |
|  | 150 | 19.6 | 85.2 | 4.6 | 8.2 | 98.5 |
|  | 152 | 23.8 | 83.3 | 5.3 | 8.2 | 97.8 |
| 330 | 160 | 17.6 | 89.9 | 2.6 | 5.2 | 98.6 |
| (pH 1.95) | 162 | 20.7 | 90.3 | 2.7 | 5.6 | 98.5 |
|  | 165 | 25.0 | 92.3 | 3.3 | 5.8 | 98.3 |
|  | 168 | 32.5 | 90.1 | 4.0 | 6.4 | 97.9 |
| 400 | 165 | 15.1 | 88.3 | 1.2 | 1.5 | 98.9 |
| (pH 2.24) | 167 | 17.5 | 89.3 | 1.6 | 2.6 | 98.7 |
|  | 169 | 19.9 | 91.7 | 1.8 | 3.5 | 98.5 |
|  | 172 | 24.8 | 91.1 | 2.6 | 3.7 | 98.0 |
| 500 | 169 | 11.52 | 89.5 | 0.8 | 2.0 | 99.1 |
| (pH 2.52) | 172 | 15.98 | 90.3 | 1.0 | 2.4 | 98.9 |
|  | 174 | 18.91 | 94.1 | 1.1 | 2.9 | 98.7 |
|  | 176 | 22.63 | 92.5 | 1.2 | 4.1 | 98.5 |

It is found that with increasing sodium content and thus increasing pH, a higher temperature is necessary to achieve the same conversion (see FIG. 6), but at the same time the selectivity achieved for HMF increases from 85% without sodium up to 94% at 500 mg/L sodium.

Example 4: HMI Synthesis with Sodium Nitrate/Nitric Add Mixtures—Influence of the Sodium Nitrate/Nitric Acid Ratio A fructose syrup with 85% fructose purity and a DM content of 75% was used as starting material. The fructose syrup was diluted with deionized water and mixed with nitric acid and sodium nitrate in the desired ratio so that the resulting solution had a dry matter content of 20% DM and a nitrate content of 0.19 wt.-% based on the total solution (corresponding to (0.03 mol/L). The nitrate/sodium ratios, the salt/acid ratio and the resulting pH values are indicated in Table 5.

TABLE 5

Nitrate contents, nitrate/sodium ratio, salt/acid
ratio and pH values and reaction temperatures used
for the reaction solutions used in Example 4.

| Test | Nitrate content [mg/L] | Sodium-content [mg/L] | Nitrate/sodium ratio [mol/mol] | Salt/acid ratio [mol/mol] | pH | Reaction temperatures [° C.] |
|---|---|---|---|---|---|---|
| 1 | 1900 | 0 | / | / | 1.44 | 145-155 |
| 2 | 1900 | 320 | 2.23 | 0.83 | 1.71 | 155-160 |
| 3 | 1900 | 450 | 1.57 | 1.77 | 1.86 | 155-165 |
| 4 | 1900 | 510 | 1.38 | 2.62 | 2.05 | 162-172 |
| 5 | 1900 | 600 | 1.17 | 5.74 | 2.50 | 160-178 |

These reaction solutions were then converted with a residence time of 5.6 min. in the head zone at the reaction temperatures indicated in Table 5 (temperature of the thermal oil). After each temperature increase, the system was given 2 hours to reach steady state.

Figure 9:
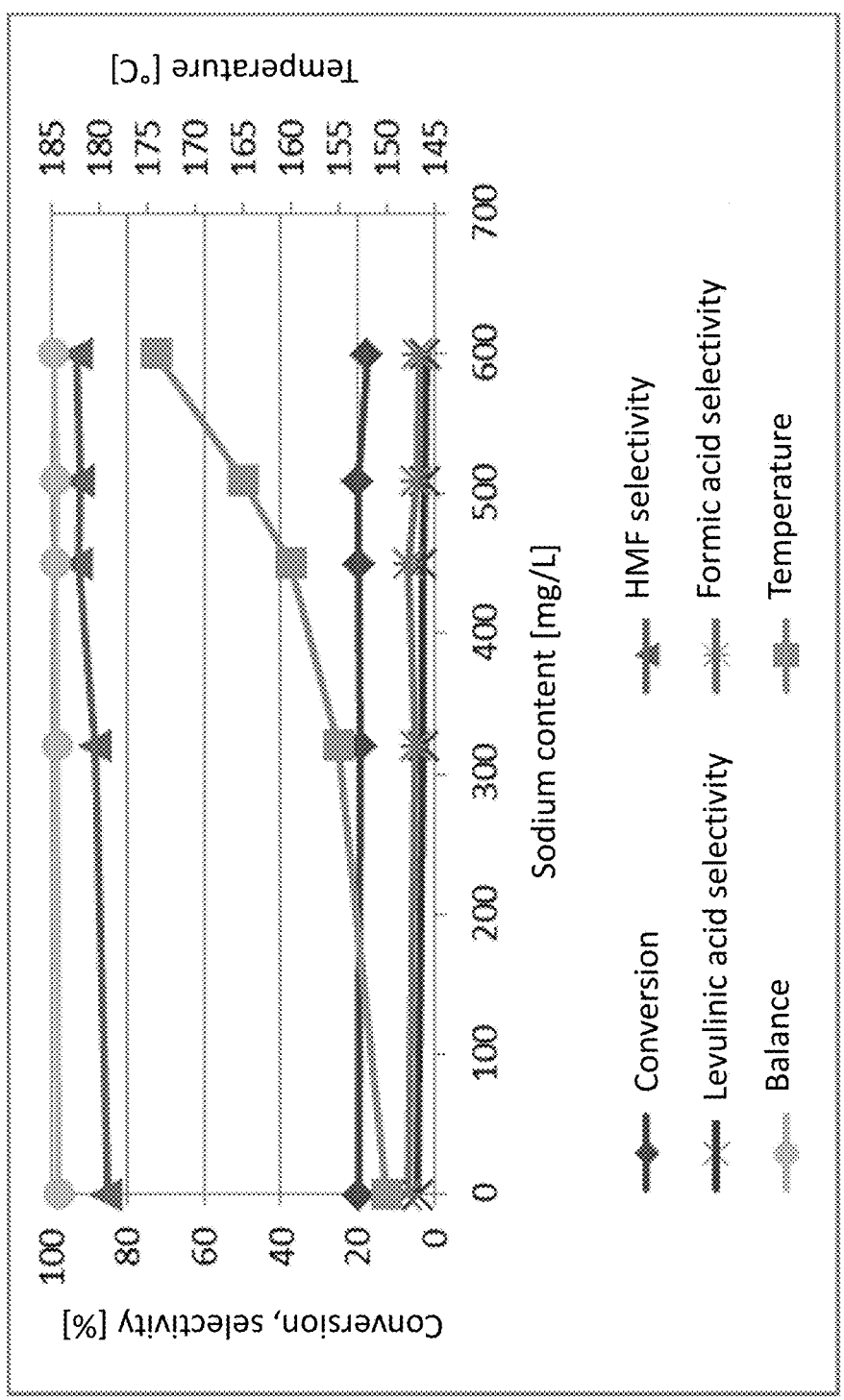
FIG. 9 shows the reaction temperatures necessary for a fructose conversion of ~20% as a function of the sodium content with a constant nitrate content as well as HMF, levulinic acid and formic acid selectivities and the balance at this point.

In FIG. 9 and Table 6, the necessary reaction temperatures and the resulting HMF, levulinic acid and formic acid selectivities and the balances are shown in each case with a fructose conversion of ~20%.

Here, too, it can be seen that with increasing sodium content and thus increasing pH, a higher temperature is necessary in order to achieve the same conversion, but at the same time the selectivity to HMF increases significantly from 86.3% (at 19.7% conversion) without sodium to 93.1% (at 17.6% conversion) at 600 mg/L sodium. The selectivities for the byproducts levulinic and formic acid are also lower in the presence of sodium, if the same conversions are compared.

TABLE 6

HMF, levulinic acid and formic acid selectivity and carbon balance at the reaction temperature required
for 18% fructose conversion, depending on the sodium content (with constant nitrate concentration).

| Sodium content [mg/L] | Temperature [° C.] | Fructose conversion [%] | HMF selectivity [%] | Levulinic acid selectivity [%] | Formic acid selectivity [%] | Balance [%] |
|---|---|---|---|---|---|---|
| 0 | 145 | 15.0 | 85.4 | 3.6 | 6.1 | 98.7 |
| (pH 1.4) | 148 | 19.7 | 86.3 | 4.2 | 7.0 | 98.0 |
|  | 150 | 21.1 | 88.4 | 5.2 | 9.8 | 97.8 |
| 320 | 155 | 19.1 | 88.3 | 2.9 | 4.9 | 98.6 |
| (pH 1.7) | 157 | 21.8 | 88.9 | 3.4 | 5.3 | 98.7 |
|  | 160 | 26.8 | 90.0 | 4.5 | 7.8 | 98.8 |

TABLE 6-continued

HMF, levulinic acid and formic acid selectivity and carbon balance at the reaction temperature required for 18% fructose conversion, depending on the sodium content (with constant nitrate concentration).

| Sodium content [mg/L] | Temperature [° C.] | Fructose conversion [%] | HMF selectivity [%] | Levulinic acid selectivity [%] | Formic acid selectivity [%] | Balance [%] |
|---|---|---|---|---|---|---|
| 450 | 155 | 14.3 | 86.9 | 1.9 | 3.2 | 98.5 |
| (pH 1.9) | 157 | 16.1 | 90.7 | 2.8 | 4.3 | 98.7 |
| | 160 | 19.7 | 92.9 | 3.2 | 6.7 | 98.9 |
| | 162 | 22.0 | 94.7 | 3.7 | 7.3 | 98.8 |
| | 165 | 30.5 | 89.1 | 4.5 | 6.8 | 98.4 |
| 510 | 162 | 15.4 | 89.7 | 1.7 | 2.9 | 98.7 |
| (pH 2.1) | 165 | 19.9 | 92.5 | 2.3 | 4.5 | 98.8 |
| | 169 | 25.7 | 92.8 | 3.1 | 5.3 | 98.8 |
| | 172 | 33.7 | 89.4 | 3.5 | 6.0 | 97.9 |
| 600 | 160 | 4.4 | 87.6 | 0.00 | 0.00 | 99.3 |
| (pH 2.50) | 165 | 8.0 | 88.0 | 1.2 | 2.9 | 99.6 |
| | 169 | 10.8 | 93.0 | 1.5 | 2.2 | 99.4 |
| | 174 | 17.6 | 93.1 | 1.9 | 4.0 | 99.4 |
| | 178 | 24.0 | 93.0 | 2.1 | 5.9 | 99.1 |

Example 5: HMF Synthesis with Hydrochloric Acid/Sodium Chloride Mixtures—Influence of the Concentration of the Acid/Salt Mixture A fructose syrup with 85% fructose purity and a DM content of 75% was used as starting material. The fructose syrup was diluted with deionized water and mixed with a mixture of hydrochloric acid and sodium chloride, which had a chloride/sodium ratio of 1.3. Various reaction solutions were prepared, all of which had a dry matter content of 20% DM and a variable acid/salt mixture concentration between 0.01 and 0.75 wt.-% based on the total solution.

These reaction solutions were then reacted with a residence time of 5.6 min. in the heating zone at the reaction temperatures indicated in Table 7 (temperature of the thermal oil). After each temperature increase, the system was given 2 hours to reach steady state.

TABLE 7

Concentration of the hydrochloric acid/sodium chloride mixture, pH values and reaction temperatures of the reaction solutions used in Example 5.

| Test | Concentration of the acid/salt mixture (HCl/NaCl) [wt.-%] | pH [—] | Reaction-temperatures [° C.] |
|---|---|---|---|
| 1 | 0.01 | 3.34 | 169-180 |
| 2 | 0.12 | 2.29 | 165-172 |
| 3 | 0.45 | 1.72 | 153-159 |
| 4 | 0.75 | 1.51 | 150-152 |

Figure 10:
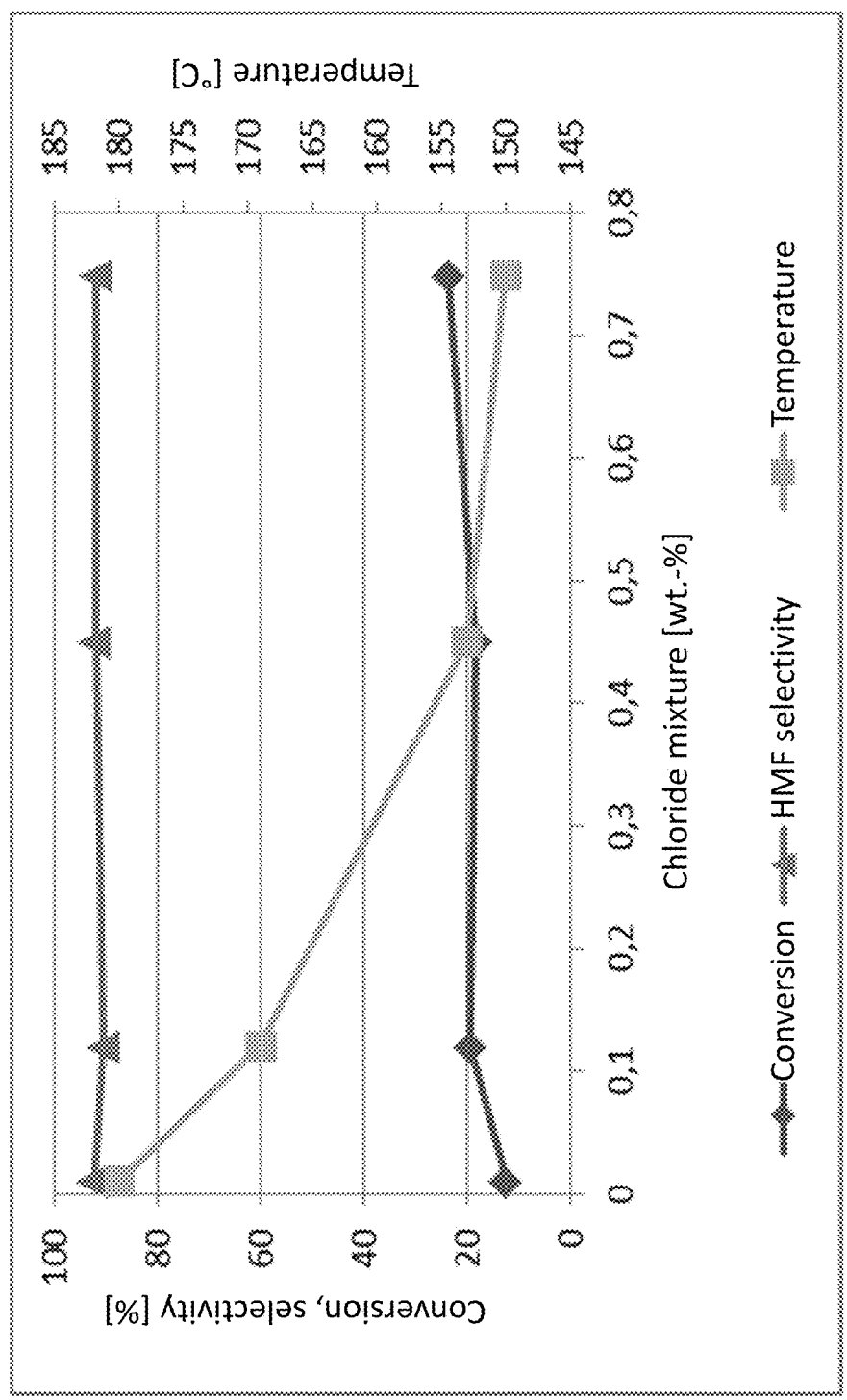
FIG. 10 shows the reaction temperatures necessary for a fructose conversion of ~20% as a function of the concentration of the salt and acid mixture with a constant chloride/sodium ratio as well as HMF, levulinic acid and formic acid selectivities and the balance at this point.

In FIG. 10 and Table 8, the necessary reaction temperatures and the resulting HMF, levulinic acid and formic acid selectivities and the balances are shown for a fructose conversion of ~20%.

TABLE 8

HMF, levulinic acid and formic acid selectivity as well as balance at different reaction temperatures depending on the concentration of the acid/salt mixture with a constant chloride/sodium ratio.

| Concentration of HCl/NaCl mixture [wt.-%] | Temperature [° C.] | Fructose conversion [%] | HMF selectivity [%] | Levulinic acid selectivity [%] | Formic acid selectivity [%] | Balance [%] |
|---|---|---|---|---|---|---|
| 0.01 | 169 | 4.6 | 91.4 | 0.0 | 0.0 | 99.5 |
| (pH 3.34) | 172 | 4.9 | 91.5 | 0.0 | 0.0 | 99.4 |
| | 176 | 7.8 | 92.5 | 0.0 | 3.0 | 99.4 |
| | 180 | 12.7 | 92.3 | 0.0 | 1.8 | 99.3 |
| 0.12 | 165 | 13.7 | 89.2 | 1.3 | 1.7 | 98.8 |
| (pH 2.29) | 169 | 19.3 | 90.4 | 1.4 | 3.6 | 98.4 |
| | 172 | 24.9 | 90.1 | 1.8 | 3.7 | 98.3 |
| 0.45 | 153 | 18.3 | 91.9 | 3.0 | 5.1 | 98.6 |
| (pH 1.72) | 155 | 21.4 | 91.9 | 3.4 | 5.4 | 98.7 |
| | 157 | 25.2 | 91.3 | 3.7 | 5.5 | 98.4 |
| | 159 | 29.6 | 90.3 | 4.3 | 6.3 | 98.0 |
| 0.75 | 150 | 23.6 | 91.7 | 4.3 | 6.8 | 98.3 |
| (pH 1.51) | 152 | 31.3 | 89.7 | 5.2 | 8.1 | 97.9 |

With increasing salt concentration, significantly lower temperatures are necessary to achieve the same conversion. It can also be seen that the high HMF selectivities of ~90% are still achieved even with high fructose conversions of >30%.

With increasing salt concentration, significantly lower temperatures are necessary to achieve the same conversion. It can also be seen that the high HMF selectivity of ~90% can still be achieved even with high fructose conversions of >37%. Even with a fructose conversion of ~47%, an HMF selectivity of ~89% is still achieved.

Example 6: HMF Synthesis with Nitric Acid/Sodium Nitrate Mixtures—Influence of the Concentration of the Acid/Salt Mixture A fructose syrup with 85% fructose purity and a DM content of 75% was used as starting material. The fructose syrup was diluted with deionized water and mixed with a mixture of nitric acid and sodium nitrate, which had a nitrate/sodium ratio of 1.2. Various reaction solutions were prepared, all of which had a dry matter content of 20% DM and a variable acid/salt mixture concentration between 0.01 and 1.5 wt.-% based on the total solution. These reaction solutions were then reacted with a residence time of 5.6 min. in the heating zone at the reaction temperatures indicated in Table 9 (temperature of the thermal oil). After each temperature increase, the system was given 2 hours to reach steady state.

TABLE 9

Concentration of the nitric acid/sodium nitrate mixture, pH values and reaction temperatures of the reaction solutions used in Example 5.

| Test | Concentration of the acid/salt mixture (HNO$_3$/NaNO$_3$) [wt.-%] | pH [—] | Reaction-temperatures [° C.] |
|---|---|---|---|
| 1 | 0.01 | 3.34 | 169-180 |
| 2 | 0.22 | 2.29 | 165-172 |
| 3 | 0.75 | 1.93 | 150-152 |
| 4 | 1.5 | 1.62 | 155-165 |

Figure 11:
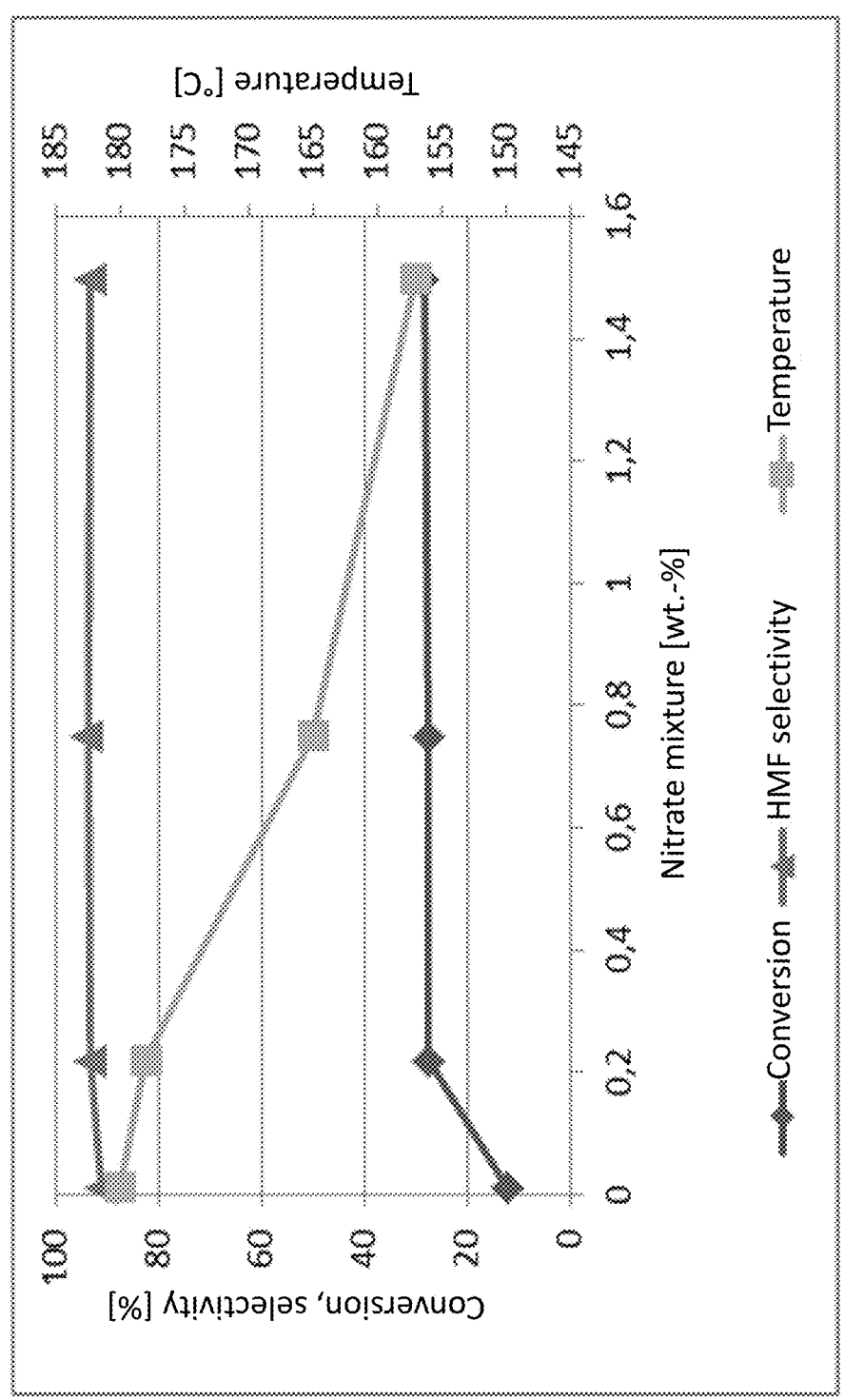
FIG. 11 shows the reaction temperatures necessary for a fructose conversion of ~27% as a function of the concentration of the salt and acid mixture with a constant nitrate/sodium ratio as well as HMF, levulinic acid and formic acid selectivities and the balance at this point.

In FIG. 11 and Table 10, the necessary reaction temperatures and the resulting HMF, levulinic acid and formic acid selectivities and the balances are shown for a fructose conversion of ~27%.

Figure 12:
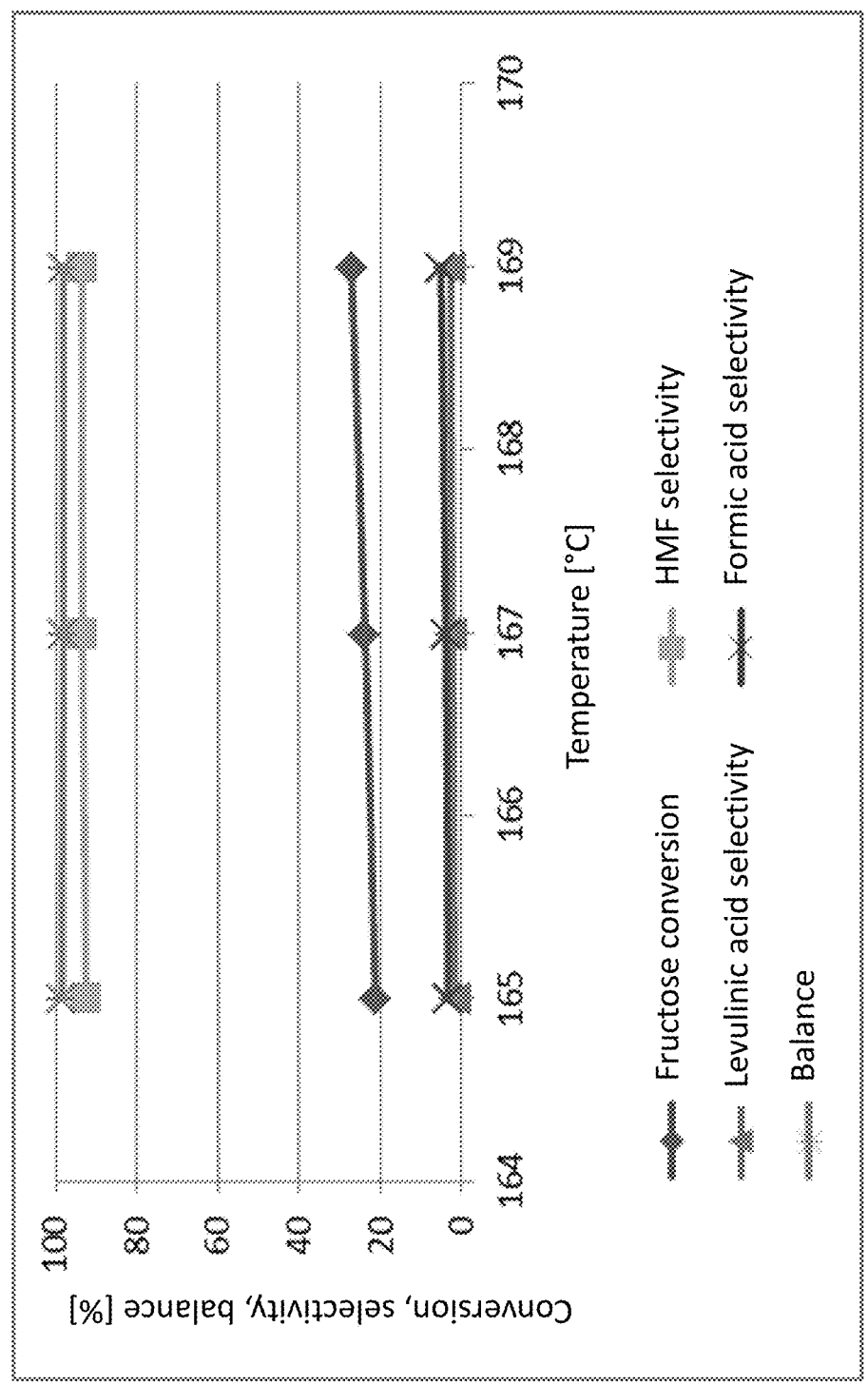
FIG. 12 shows the HMF synthesis with 20% DM KH (85% fructose purity) and 0.12 wt.-% $HCl/CaCl_2$ at temperatures of 165-169° C. Fructose conversion, HMF, levulinic acid and formic acid selectivity and the balance are represented.

Example 7: HMF Synthesis with 0.11 wt.-% Hydrochloric Acid/Calcium Chloride Mixture A fructose syrup with 85% fructose purity and a DM content of 75% was used as starting material. The fructose syrup was diluted with deionized water and mixed with a mixture of hydrochloric acid and calcium chloride, which resulted in the same amount of free acid as in Example 5 with 0.12 wt.-% HCl/NaCl, Table 7, Test 2. The pH of the reaction solution was 2.08. This reaction solution was then reacted with a residence time of 5.6 min. in the heating zone at a temperature of 165° C.-169° C. (temperature of the thermal oil). After each temperature increase, the system was given 2 hours to reach steady state. The results on fructose conversion, HMF, levulinic acid and formic acid selectivity and balance are shown in FIG. 12 and Table 11.

TABLE 10

HMF, levulinic acid and formic acid selectivity as well as balance at different reaction temperatures depending on the concentration of the acid/salt mixture with a constant nitrate/sodium ratio.

| Concentration of HNO$_3$/NaNO$_3$ mixture [wt.-%] | Temperature [° C.] | Fructose conversion [%] | HMF selectivity [%] | Levulinic acid selectivity [%] | Formic acid selectivity [%] | Balance [%] |
|---|---|---|---|---|---|---|
| 0.01 | 165 | 2.2 | 86.1 | 0.0 | 0.0 | 99.7 |
| (pH 3.34) | 172 | 4.9 | 87.6 | 0.0 | 0.0 | 99.8 |
|  | 176 | 7.5 | 91.6 | 0.0 | 1.5 | 99.5 |
|  | 180 | 12.2 | 91.0 | 0.0 | 1.9 | 99.6 |
| 0.22 | 169 | 14.2 | 91.1 | 1.7 | 3.6 | 99.4 |
| (pH 2.29) | 172 | 18.3 | 91.6 | 1.3 | 2.4 | 99.5 |
|  | 174 | 21.8 | 92.6 | 1.0 | 2.5 | 99.3 |
|  | 174 | 24.1 | 94.8 | 1.4 | 3.2 | 98.4 |
|  | 178 | 27.6 | 93.2 | 1.7 | 3.2 | 97.9 |
| 0.75 | 165 | 27.5 | 93.8 | 3.2 | 5.5 | 98.3 |
| (pH 1.93) | 169 | 37.9 | 90.1 | 4.1 | 7.3 | 97.4 |
| 1.5 | 155 | 24.6 | 93.2 | 4.1 | 6.6 | 98.0 |
| (pH 1.62) | 157 | 28.4 | 93.2 | 4.7 | 7.7 | 97.9 |
|  | 165 | 46.7 | 88.9 | 6.3 | 9.8 | 97.1 |

TABLE 11

Fructose conversion, HMF, levulinic acid and formic acid selectivity and carbon balance as a function of the reaction temperature when using 0.12 wt.-% HCl/CaCl$_2$.

| Temperature [° C.] | Fructose conversion [%] | HMF selectivity [%] | Levulinic acid selectivity [%] | Formic acid selectivity [%] | Balance [%] |
|---|---|---|---|---|---|
| 165 | 21.2 | 92.5 | 1.7 | 3.3 | 98.5 |
| 167 | 23.8 | 93.4 | 2.3 | 3.9 | 98.2 |
| 169 | 27.2 | 93.5 | 2.7 | 5.1 | 98.2 |

Figure 13:
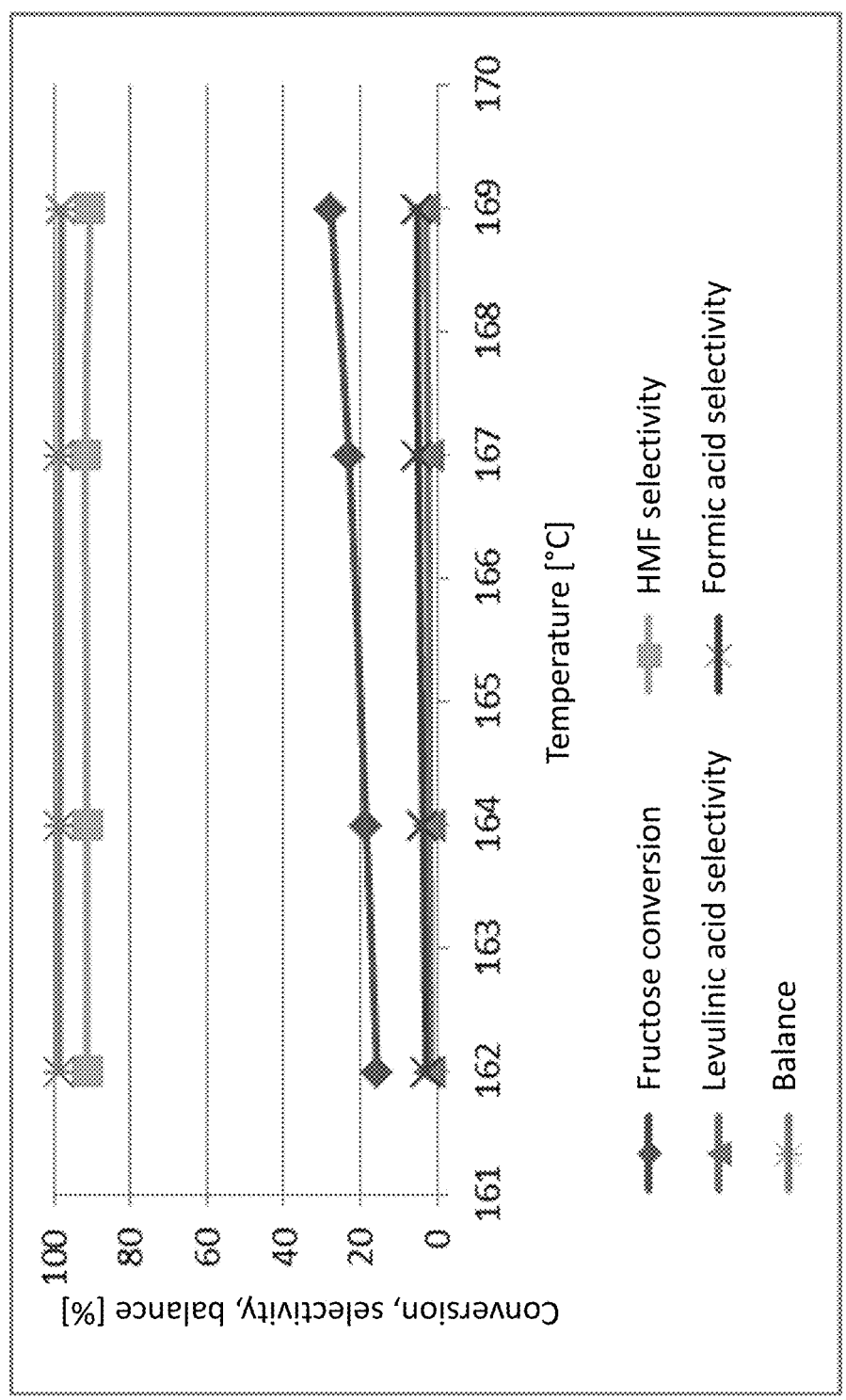
FIG. 13 shows the HMF synthesis with 20% DM KH (85% fructose purity) and 0.12 wt.-% $HCl/MgCl_2$ at temperatures of 162-169° C. Fructose conversion, HMF, levulinic acid and formic acid selectivity and the balance are represented.

Example 8: HMF Synthesis with 0.12 wt.-% Hydrochloric Acid/Magnesium Chloride Mixture A fructose syrup with 85% fructose purity and a DM content of 75% was used as starting material. The fructose syrup was diluted with deionized water and mixed with a mixture of hydrochloric acid and magnesium chloride, which resulted in the same amount of free acid as in Example 5 with 0.12 wt.-% HCl/NaCl, Table 7, Test 2. The pH of the reaction solution was 2.09. This reaction solution was then converted with a residence time of 5.6 min. in the heating zone at a temperature of 162° C.-169° C. (temperature of the thermal oil). After each temperature increase, the system was given 2 hours to reach steady state. The results on fructose conversion, HMF, levulinic acid and formic acid selectivity and balance are shown in FIG. 13 and Table 12.

TABLE 12

Fructose conversion, HMF, levulinic acid and formic acid selectivity as well as the balance depending on the reaction temperature when using 0.12 wt.-% HCl/MgCl$_2$.

| Temperature [° C.] | Fructose conversion [%] | HMF selectivity [%] | Levulinic acid selectivity [%] | Formic acid selectivity [%] | Balance [%] |
|---|---|---|---|---|---|
| 162 | 15.7 | 91.3 | 1.7 | 2.9 | 98.6 |
| 164 | 18.6 | 91.4 | 2.0 | 3.7 | 98.5 |
| 167 | 23.1 | 91.8 | 2.4 | 5.0 | 98.4 |
| 169 | 27.8 | 90.5 | 3.0 | 5.0 | 97.9 |

Examples 7 and 8 show that the positive effects with regard to the high HMF selectivities are also achieved when using other cations (here calcium and magnesium).

The invention claimed is:

1. A method for the production of 5-hydroxymethylfurfural (HMF) comprising the following steps:
   a) providing a fructose-containing component and a catalyst system comprising a solution of a salt and acid mixture,
   b) mixing the fructose-containing component with the catalyst system to obtain a reaction solution,
   c) converting the fructose present in the reaction solution to HMF at a temperature of 90° C. to 200° C. to obtain a liquid HMF-containing product mixture and
   d) obtaining a liquid HMF-containing product mixture, wherein no organic solvent is used in steps a) to d) and the salt is an alkaline or alkaline earth metal salt.

2. The method according to claim 1, wherein the acid is a mineral acid and/or an organic acid and the salt is a salt of a mineral acid and/or an organic acid.

3. The method according to claim 1, wherein the mineral acid is selected in particular from the group consisting of hydrochloric acid, sulfuric acid, nitric acid and phosphoric acid; and the organic acid is selected in particular from the group consisting of acetic acid, citric acid, tartaric acid, oxalic acid, glycolic acid and gluconic acid.

4. The method according to claim 1, wherein the salt of a mineral acid is selected from the group consisting of alkaline halides, alkaline earth halides, alkaline nitrates, alkaline earth nitrates, alkaline sulfates, alkaline earth sulfates, alkaline phosphates, alkaline earth phosphates and mixtures thereof; and the salt of an organic acid is selected in particular from the group consisting of acetates, citrates, tartrates, oxalates, glycolates, gluconates and mixtures thereof.

5. The method according to claim 1, wherein the concentration of the salt and acid mixture is 0.01 to 2.00 wt.-% (based on the total weight of the reaction solution obtained in method step b)).

6. The method according to claim 1, wherein the pH of the reaction solution obtained in method step b) is 1.2 to 4.5.

7. They method according to claim 1, wherein in method step b) a reaction solution with a carbohydrate content of 5 to 50 wt.-% (dry matter carbohydrate in relation to the total weight of the reaction solution) is obtained and used in method step c).

8. The method according to claim 1, wherein in method step b) a reaction solution with a fructose content of 40 to 100 wt.-% (dry matter fructose in relation to dry matter carbohydrate) is obtained and used in method step c).

9. The method according to claim 1, wherein the fructose-containing component is a solid fructose-containing component, in particular fructose, or a liquid fructose-containing component, in particular a fructose syrup or a fructose solution.

10. The method according to claim 1, wherein the ratio of salt to free acid in the reaction solution obtained in method step b) is 0.8 to 10 (mol/mol).

11. The method according to claim 1, wherein the ratio of anions of the salt and acid mixture to cations of the salt of the salt and acid mixture in the reaction solution obtained in method step b) is 0.5 to 4 (mol/mol).

12. The method according to claim 1, wherein the concentration of anions of the catalyst system in the reaction solution obtained in method step b) is $1 \times 10^{-5}$ to 0.6 mol/L.

13. The method according to claim 1, wherein the fructose-containing component provided in method step a), the catalyst system or both are set to a temperature of 90° C. to 200° C. before method step b) or wherein the reaction solution obtained in method step b) is set to a temperature of 90° C. to 200° C.

14. The method according to claim 1, wherein the process is carried out such that a fructose conversion of 1 to 50 mol-% is achieved in method step c).

15. The method according to claim 1, wherein the method is set so that in method step c) an HMF selectivity of 60 to 100 mol-% is obtained.

16. The method according to claim 1, wherein apart from the catalyst system, no further catalytically active component is used in the process.

17. The method according to claim 1, comprising the following step:
   e) cooling the liquid HMF product mixture to a temperature of 20° to 80° C.

18. The method according to claim 1, comprising the following step:
   f) filtration, decolorization and/or purification of the liquid HMF product mixture.

19. The method according to claim 1, comprising the following step:
   g) setting the liquid HMF product mixture to a dry matter content of 20 to 70 wt.-%.

20. The method according to claim 1, comprising the following steps:
   h) purification of the liquid HMF product mixture using chromatography, ultra- and/or nanofiltration, extraction with a suitable extractant, adsorption on a suitable material and subsequent targeted desorption and/or electrodialysis to separate at least one HMF fraction, and
   i) obtaining at least one HMF fraction.

21. The method according to claim 20, wherein the liquid HMF product mixture is separated in step h) using chromatography into at least four fractions comprising an HMF fraction, a glucose fraction, a fructose fraction and an organic acid fraction, and in step i) at least an HMF fraction, a glucose fraction, a fructose fraction and an organic acid fraction are obtained.

22. The method according to claim 21, wherein the fructose fraction obtained in method step i) is recycled into step a).

23. The method according to claim 21, wherein the glucose fraction obtained in method step i) is used for the production of ethanol.

24. The method according to claim 21, wherein the organic acid fraction obtained in method step i) is used to isolate levulinic and formic acid.

25. The method according to claim 21, wherein the HMF fraction obtained in method step i) is oxidized directly and is oxidized in a further step to 2,5-furandicarboxylic acid (FDCA) without the need for further purification.

* * * * *